US010711317B2

(12) United States Patent
Norman et al.

(10) Patent No.: US 10,711,317 B2
(45) Date of Patent: *Jul. 14, 2020

(54) DETECTION OF NUCLEIC ACIDS FROM MULTIPLE TYPES OF HUMAN PAPILLOMAVIRUS

(71) Applicant: GEN-PROBE INCORPORATED, San Diego, CA (US)

(72) Inventors: Sylvia A. Norman, Poway, CA (US); Jennifer J. Bungo, San Diego, CA (US); William L. Hanna, San Diego, CA (US); Neeraj P. Rao, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/582,744

(22) Filed: Sep. 25, 2019

(65) Prior Publication Data
US 2020/0032355 A1    Jan. 30, 2020

Related U.S. Application Data

(60) Continuation of application No. 16/040,847, filed on Jul. 20, 2018, which is a division of application No. 14/747,974, filed on Jun. 23, 2015, now Pat. No. 10,047,407, which is a continuation of application No. 14/451,263, filed on Aug. 4, 2014, now Pat. No. 9,074,263, which is a division of application No. 14/041,970, filed on Sep. 30, 2013, now Pat. No. 8,835,114, which is a continuation of application No. 14/040,399, filed on Sep. 27, 2013, now Pat. No. 8,785,125, which is a continuation of application No. 13/678,402, filed on Nov. 15, 2012, now Pat. No. 8,574,841, which is a continuation of application No. 13/216,107, filed on Aug. 23, 2011, now Pat. No. 8,334,098, which is a continuation of application No. 12/643,934, filed on Dec. 21, 2009, now Pat. No. 8,026,066, which is a continuation of application No. 11/926,984, filed on Oct. 29, 2007, now Pat. No. 7,682,792, which is a continuation of application No. 11/296,931, filed on Dec. 8, 2005, now Pat. No. 7,354,719.

(60) Provisional application No. 60/634,458, filed on Dec. 8, 2004.

(51) Int. Cl.
C12Q 1/70         (2006.01)
C07K 14/005    (2006.01)

(52) U.S. Cl.
CPC .......... *C12Q 1/708* (2013.01); *C07K 14/005* (2013.01); *C12N 2710/20022* (2013.01); *C12Q 2600/156* (2013.01); *C12Q 2600/158* (2013.01); *C12Q 2600/16* (2013.01)

(58) Field of Classification Search
CPC .............. C12Q 1/708; C12Q 2600/156; C12Q 2600/16; C12N 2710/20022; C07K 14/025

See application file for complete search history.

(56) References Cited

U.S. PATENT DOCUMENTS

| | | |
|---|---|---|
| 4,849,331 A | 7/1989 | Lorinez |
| 4,849,332 A | 7/1989 | Lorinez |
| 4,849,334 A | 7/1989 | Lorinez |
| 4,908,306 A | 3/1990 | Lorinez |
| 4,983,728 A | 1/1991 | Herzog et al. |
| 5,030,557 A | 7/1991 | Hogan et al. |
| 5,182,377 A | 1/1993 | Manos et al. |
| 5,283,171 A | 2/1994 | Manos et al. |
| 5,342,930 A | 8/1994 | Orth et al. |
| 5,411,857 A | 5/1995 | Beaudenon et al. |
| 5,447,839 A | 9/1995 | Manos et al. |
| 5,484,699 A | 1/1996 | Bouma et al. |
| 5,527,898 A | 6/1996 | Bauer et al. |
| 5,534,439 A | 7/1996 | Orth et al. |
| 5,554,538 A | 9/1996 | Cole et al. |
| 5,597,910 A | 1/1997 | Gudibande et al. |
| 5,639,871 A | 6/1997 | Bauer et al. |
| 5,643,715 A | 7/1997 | Lancaster |
| 5,654,142 A | 8/1997 | Kievits et al. |
| 5,654,416 A | 8/1997 | Cummins et al. |
| 5,656,423 A | 8/1997 | Orth et al. |
| 5,665,571 A | 9/1997 | Beaudenon et al. |
| 5,679,509 A | 10/1997 | Wheeler et al. |

(Continued)

FOREIGN PATENT DOCUMENTS

| | | |
|---|---|---|
| EP | 0 334 694 A1 | 9/1989 |
| EP | 0 402 132 A2 | 12/1990 |

(Continued)

OTHER PUBLICATIONS

Sotlar et al., "Detection and Typing of Human Papillomavirus by E6 Nested Multiplex PCR", Journal of Clinical Microbiology, 2004, vol. 42, No. 7, pp. 3176-3184.
USPTO Notice of Allowance, U.S. Appl. No. 14/748,035, dated May 22, 2017.
Majlessi et al., "Advantages of 2'-O-methyl oligoribonucleotide probes for detecting RNA targets," Nucleic Acids Res., 1998, 26(9):2224-2229, Oxford Univ. Press, U.S.
USPTO Non-Final Rejection, U.S. Appl. No. 14/747,974, dated Aug. 11, 2017.

(Continued)

*Primary Examiner* — David C Thomas
(74) *Attorney, Agent, or Firm* — Nicholas V. Sherbina; Jeffrey E. Landes

(57) ABSTRACT

Nucleic acid oligonucleotide sequences are disclosed which include amplification oligomers and probe oligomers which are useful for detecting multiple types of human papillomaviruses (HPV) associated with cervical cancer. Methods for detecting multiple HPV types in biological specimens by amplifying HPV nucleic acid sequences in vitro and detecting the amplified products are disclosed.

24 Claims, 1 Drawing Sheet

Specification includes a Sequence Listing.

(56) References Cited

U.S. PATENT DOCUMENTS

| | | |
|---|---|---|
| 5,695,926 A | 12/1997 | Cros et al. |
| 5,705,627 A | 1/1998 | Manos et al. |
| 5,712,092 A | 1/1998 | Orth et al. |
| 5,750,334 A | 5/1998 | Cerutti et al. |
| 5,783,412 A | 7/1998 | Manos et al. |
| 5,824,466 A | 10/1998 | Orth et al. |
| 5,840,306 A | 11/1998 | Hofmann et al. |
| 5,876,922 A | 3/1999 | Orth et al. |
| 5,932,451 A | 8/1999 | Wang et al. |
| 5,952,487 A | 9/1999 | Philipp et al. |
| 5,958,674 A | 9/1999 | Beaudenon et al. |
| 5,981,173 A | 11/1999 | Orth et al. |
| 5,985,610 A | 11/1999 | Lowy et al. |
| 6,013,258 A | 1/2000 | Urban et al. |
| 6,013,262 A | 1/2000 | Frazer et al. |
| 6,027,891 A | 2/2000 | Von Knebel-Doberitz et al. |
| 6,107,086 A | 8/2000 | Cole et al. |
| 6,159,729 A | 12/2000 | Hofmann et al. |
| 6,218,104 B1 | 4/2001 | Morris et al. |
| 6,228,368 B1 | 5/2001 | Gissmann et al. |
| 6,235,523 B1 | 5/2001 | Gajewczyk et al. |
| 6,242,250 B1 | 6/2001 | Cole et al. |
| 6,290,965 B1 | 9/2001 | Jansen et al. |
| 6,306,397 B1 | 10/2001 | Edwards et al. |
| 6,313,373 B1 | 11/2001 | Eckert et al. |
| 6,352,696 B1 | 3/2002 | Hallek et al. |
| 6,355,424 B1 | 3/2002 | Lorincz |
| 6,406,850 B2 | 6/2002 | Volkers et al. |
| 6,582,908 B2 | 6/2003 | Fodor et al. |
| 6,583,278 B1 | 6/2003 | Carter |
| 6,902,899 B2 | 6/2005 | Iftner |
| 6,936,443 B2 | 8/2005 | Cohenford et al. |
| 7,063,963 B2 | 6/2006 | Cole et al. |
| 7,288,258 B2 | 10/2007 | Choppin et al. |
| 7,354,719 B2 | 4/2008 | Norman et al. |
| 7,355,034 B2 | 4/2008 | Gordon et al. |
| 7,470,512 B2 | 12/2008 | Gordon et al. |
| 7,524,631 B2 | 4/2009 | Patterson |
| 7,527,948 B2 | 5/2009 | Hudson et al. |
| 7,553,623 B2 | 6/2009 | Karlsen |
| 7,645,571 B2 | 1/2010 | Anthony et al. |
| 7,682,792 B2 | 3/2010 | Norman et al. |
| 8,026,066 B2 | 9/2011 | Norman et al. |
| 8,334,098 B2 * | 12/2012 | Norman .................. C12Q 1/708 435/6.1 |
| 8,574,841 B2 * | 11/2013 | Norman ................ C07K 14/005 435/6.1 |
| 8,785,125 B2 * | 7/2014 | Norman .................. C12Q 1/708 435/6.1 |
| 8,835,114 B2 * | 9/2014 | Norman ................ C07K 14/005 435/6.1 |
| 9,074,263 B2 * | 7/2015 | Norman .................. C12Q 1/708 |
| 9,328,392 B2 * | 5/2016 | Norman .................. C12Q 1/708 |
| 10,047,407 B2 | 8/2018 | Norman et al. |
| 2001/0053519 A1 | 12/2001 | Fodor et al. |
| 2004/0018539 A1 | 1/2004 | Gordon et al. |
| 2004/0101533 A1 | 5/2004 | Muller et al. |
| 2004/0214302 A1 | 10/2004 | Anthony et al. |
| 2005/0031636 A1 | 2/2005 | Gissman et al. |
| 2005/0118568 A1 | 6/2005 | Karlsen |
| 2005/0244813 A1 | 11/2005 | Karlsen |
| 2005/0249745 A1 | 11/2005 | Hallek et al. |
| 2005/0260562 A1 | 11/2005 | Gordon et al. |
| 2006/0014926 A1 | 1/2006 | Cassetti et al. |
| 2006/0029943 A1 | 2/2006 | Hermonat et al. |
| 2006/0051809 A1 | 3/2006 | Nazarenko et al. |
| 2006/0057561 A1 | 3/2006 | Hart |
| 2006/0068417 A1 * | 3/2006 | Becker .................. C12Q 1/6834 435/6.11 |
| 2006/0134615 A1 | 6/2006 | Linder et al. |
| 2006/0160069 A1 | 7/2006 | Chau et al. |
| 2006/0233770 A1 | 10/2006 | Ambinder et al. |
| 2006/0275784 A1 | 12/2006 | Light et al. |
| 2007/0031828 A1 | 2/2007 | Colau et al. |
| 2007/0037137 A1 | 2/2007 | Gyllensten et al. |
| 2007/0111960 A1 | 5/2007 | Stender et al. |
| 2019/0002995 A1 | 1/2019 | Norman et al. |

FOREIGN PATENT DOCUMENTS

| | | |
|---|---|---|
| EP | 1 018 555 A2 | 7/2000 |
| EP | 1 288 296 A2 | 3/2003 |
| EP | 1 155 153 B1 | 1/2006 |
| JP | 05192200 A | 8/1993 |
| JP | 2001 321168 A | 11/2001 |
| WO | 89 02934 A1 | 4/1989 |
| WO | 9002821 A1 | 3/1990 |
| WO | 91/08312 | 6/1991 |
| WO | 94/26934 A2 | 11/1994 |
| WO | 0129233 A3 | 4/2001 |
| WO | 01042467 A3 | 6/2001 |
| WO | 02 08460 A2 | 1/2002 |
| WO | 03/020976 | 3/2003 |
| WO | 03057914 A2 | 7/2003 |
| WO | 20040030636 A3 | 4/2004 |

OTHER PUBLICATIONS

USPTO Final Rejection, U.S. Appl. No. 14/747,974, dated Oct. 30, 2017.
USPTO Advisory Action, U.S. Appl. No. 14/747,974, dated Dec. 7, 2017.
USPTO Final Rejection, U.S. Appl. No. 14/747,974, dated Feb. 1, 2018.
USPTO Notice of Allowance, U.S. Appl. No. 14/747,974, dated Apr. 9, 2018.
JPO Office Action, Japanese Patent Application No. 2017-071621, dated Nov. 29, 2018.
JPO Notice of Allowance, Japanese Patent Application No. 2017-071621, dated Jun. 19, 2019.
de Villers et al., "Classifications of papillomaviruses", Virology, 2004, 1324:7-27, Elsevier, U.S.
Fujinaga et al., "Simultaneous detection and typing of genital human papillomavirus DNA using the polymerase chain reaction." J. Gen. Virol., May 1991, 72 (pt 5), pp. 1039-1044.
Notice of Allowance and allowed claims, Japanese Application No. 2007-545597, dated May 18, 2012.
Non-final Rejection, U.S. Appl. No. 13/216,107, dated Apr. 6, 2012.
Notice of Allowance and Fee(s) Due, U.S. Appl. No. 13/216,107, dated Aug. 20, 2012.
Corrected Notice of Allowance and Fee(s) Due, U.S. Appl. No. 13/216,107, dated Sep. 4, 2012.
Non-final Rejection, U.S. Appl. No. 13/678,402, dated Mar. 18, 2013.
Notice of Allowance and Fee(s) Due, U.S. Appl. No. 13/678,402, dated Jul. 19, 2013.
Non-final Rejection, U.S. Appl. No. 14/041,970, dated Mar. 12, 2014.
Notice of Allowance and Fee(s) Due, U.S. Appl. No. 14/041,970, dated Jun. 16, 2014.
Merriam Webster combination, attached, accessed Sep. 24, 2014.
Dictionary combination, attached, accessed Sep. 24, 2014, available at http://dictionary.reference.com/browse/combine.
Merriam Webster mixture, attached, accessed Sep. 24, 2014.
About mixture, attached, accessed Sep. 24, 2014. avail at http://chemistry.about.com/od/dictionariesglossaries/g/defmixture.htm.
Dictionary mixture, attached, accessed Sep. 24, 2014.
Merriam Webster reaction, attached, accessed Sep. 24, 2014.
Dictionary reaction, attached, accessed Sep. 24, 2014, available at http://dictionary.reference.com/browse/reaction.
USPTO Office Action, U.S. Appl. No. 12/643,934, dated Jul. 12, 2010.
USPTO Final Office Action, U.S. Appl. No. 12/643,934, dated Feb. 22, 2011.
USPTO Interview Summary, U.S. Appl. No. 12/643,934, dated Apr. 28, 2011.

(56) References Cited

OTHER PUBLICATIONS

USPTO Notice of Allowance, U.S. Appl. No. 12/643,934, dated May 18, 2011.
USPTO Notice of Allowance, U.S. Appl. No. 12/643,934, dated Jul. 28, 2011.
Extended EP Search Report for EP Patent Application 05853253.2 dated Aug. 3, 2009 (16 pages).
JPO Office Action (Translation), Japanese Patent Application No. 2007-545597, dated Mar. 29, 2011.
APO Examiner's First Report, Australian Patent Application No. 2010201656, dated Oct. 31, 2011.
CIPO Office Action, Canadian Patent Application No. 2,588,581, dated Nov. 19, 2009.
CIPO Notice of Allowance, Canadian Patent Application No. 2,588,581, dated Dec. 29, 2010.
PCT Written Opinion, International Application No. PCT/US05/44291, dated Mar. 31, 2008.
PCT International Search Report, International Application No. PCT/US05/44291, dated Mar. 31, 2008.
PCT International Preliminary Report on Patentability, International Application No. PCT/US05/44291, dated Jun. 5, 2008.
JPO Office Action (Translation), Japanese Patent Application No. 2007-545597, dated Nov. 21, 2011.
EPO Decision to Grant, European Patent Application No. 05853253.2, dated Jul. 8, 2010.
APO Examiner's First Report, Australian Patent Application No. 2005314061, dated May 4, 2009.
APO Notice of Acceptance, Australian Patent Application No. 2005314061, dated Jan. 13, 2010.
Buck et al, "Design Strategies and Performance of Custom DNA Sequencing Primers," Biotechniques. 1999. 27(3): pp. 528-536.
Dallaire et al. "Synthesis of new building blocks: Towards the analogs of peptide nucleic acids (PNAs)," Tetrahedron Letters, vol. 39, Issue 29, Jul. 16, 1998, pp. 5129-5132.
Dopazo et al. "A computer program for the design of PCR primers for diagnosis of highly variable genomes," J. Virol. Meth., 1993, vol. 41, pp. 157-166 (Elsevier Science Publishers B.V.).
Hantz, S. et al. "Hybrid Capture® 2 vs HPV Consensus kit®: Comparison of 2 assays for human papillomavirus detection and typing," Pathologie Biologie, 2005, pp. 556-562, vol. 53, Elsevier (France)—English Translation 12 pp.
McNicol et al. "Detection of Human Papillomavirus DNA in Prostate Gland Tissue by Using the Polymerase Chain Reaction Amplification Assay," J. Clin. Microbiol., 1993, vol. 28, No. 3, pp. 409-412 (American Society for Microbiology, USA).
Smits, H.L., et al. "Application of the NASBA nucleic acid amplification method for the detection of human papillomavirus type 16 E6-E7 transcripts," J. Virological Methods, 1995, pp. 75-81, vol. 54, Elsevier Science B.V.
Stratagene "Gene Characterization Kits" 1988.
Clavel et al., "DNA-EIA to detect high and low risk HPV genotypes in cervical lesions with E6/E7 primer mediated multiplex PCR," J. Clin. Path., Jan. 1998, pp. 38-43, vol. 51(1), BMJ Publishing Group, London, UK.
Sasagawa et al., "A New PCR-Based Assay Amplifies the E6-E7 Genes of Most Mucosal Human Papillomavirus (HPV)," Virus Research, 2000, pp. 127-139, vol. 67, Elsevier Science Ltd., London, UK.
Moberg et al., "Real-Time PCR-Based System for Simultaneous Quantification of Human Papillomavirus Types Associated With High Risk of Cervical Cancer," J. Clin. Microbiol., Jul. 2003, pp. 3221-3228, vol. 41 (7), American Society for Microbiology, Washington, D.C.
Sotlar et al., "Detection and Typing of Human Papillomavirus by E6 Nested Multiplex PCR," J. Clin. Microbiol., Jul. 2004, pp. 3176-3184, vol. 42(7), American Society for Microbiology, Washington, D.C.
Brestovac et al., "Multiplex Nested PCR (MNP) Assay for the Detection of 15 High Risk Genotypes of Human Papillomavirus," J. Clin. Virology, Jun. 2005, pp. 116-122, vol. 33(2), Elsevier Science Ltd., Amsterdam, NL.
Lorincz, et al., "Cloning and Characterization of the DNA of a New Human Papillomavirus from a Woman with Dysplasia of the Uterine Cervix" J. Virol., (Apr. 1986), pp. 225-229, vol. 58, No. 1, Am. Society Microbiology, Washington D.C., USA.
Shimoda, et al., "Human Papillomavirus Type 52: a New Virus Associated with Cervical Neoplasia" J. gen. Virol., (1988), pp. 2925-2928, vol. 69, Society for General Microbiology, Reading, UK.
Yajima, et al., "Isolation of a New Type of Human Papillomavirus (HPV52b) with a Transforming Activity from Cervical Cancer Tissue" Cancer Research, (Dec. 15, 1988), pp. 7164-7172, vol. 48, American Association for Cancer D Research, Philadelphia, PA.
Lorincz, et al., "Cloning and Partial DNA Sequencing of Two New Human Papillomavirus Types Associated with Condylomas and Low-Grade Cervical Neoplasia" J. Virol., (Jun. 1989), pp. 2829-2834, vol. 63, No. 6, Am. Society Microbiology, Washington D.C., USA.
Gregoire, et al., "Amplification of Human Papillomavirus DNA Sequences by Using Conserved Primers" J. Clin. Microbiol., (Dec. 1989), pp. 2660-2665, vol. 27, No. 12, Am. Society Microbiology, Washington D.C., USA.
Van Den Brule, et al., "General Primer Polymerase Chain Reaction in Combination with Sequence Analysis for Identification of Potentially Novel Human Papillomavirus Genotypes in Cervical Lesions" J. Clin. Microbiol., (Jul. 1992), pp. 1716-1721, vol. 30, No. 7, Am. Society Microbiology, Washington D. C., USA.
Farthing, et al., "Human Papillomavirus detection by hybrid capture and its possible clinical use" J. Clin. Pathol., (1994), pp. 649-652, vol. 47, BMJ Publishing Group Ltd., London, UK.
Pirami, et al., "Analysis of HPV 16, 18, 31, and 35 DNA in pre-invasive and invasive lesions of the uterine cervix" J. Clin. Pathol., (1997), pp. 600-604, vol. 50, BMJ Publishing Group Ltd., London, UK.
Nindl, et al., "Distribution of 14 high risk HPV types in cervical intraepithelial neoplasia detected by a non-radioactive General primer PCR mediated enzyme immunoassay" J. Clin. Pathol., (1999), pp. 17-22, vol. 52, BMJ Publishing Group Ltd., London, UK.
Konya, et al., "Additional Human Papillomavirus Types Detected by the Hybrid Capture Tube Test among Samples from Women with Cytological and Colposcopical Atypia" J. Clin. Microbiol., (Jan. 2000), pp. 408-411, vol. 38, No. 1, Am. Society Microbiology, Washington D.C., USA.
Yukako et al., "Simultaneous detection and typing of genital human papillomavirus DNA using the polymerase chain reaction," J. Gen. Virol., 1991, 72 (Pt.5):1039-1044, Great Britain.

* cited by examiner

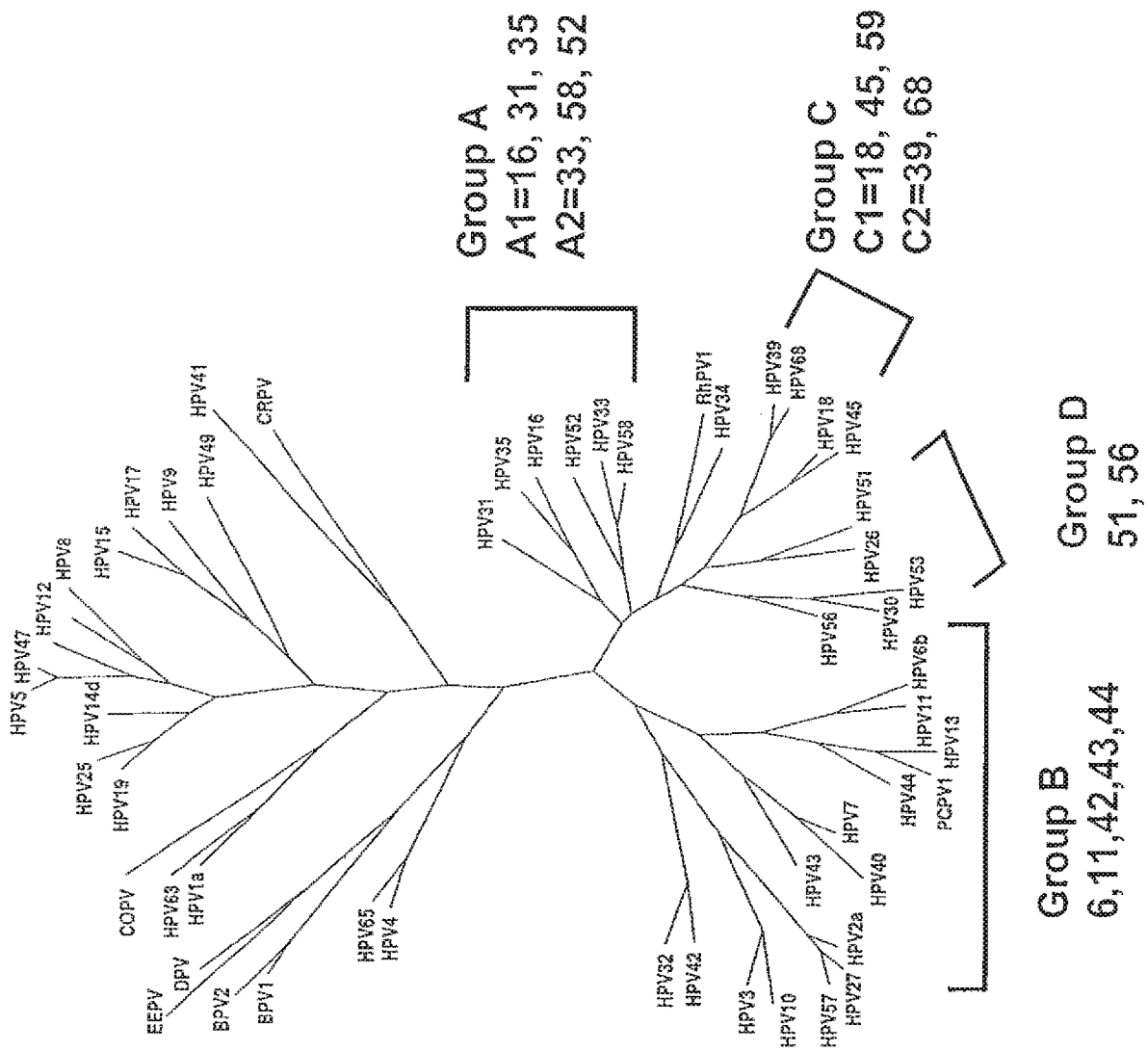

DETECTION OF NUCLEIC ACIDS FROM MULTIPLE TYPES OF HUMAN PAPILLOMAVIRUS

DOMESTIC PRIORITY DATA

This application is a CON of U.S. application Ser. No. 16/040,847 filed on Jul. 20, 2018, which is a DIV of U.S. application Ser. No. 14/747,974 filed on Jun. 23, 2015, now U.S. Pat. No. 10,047,407, which is a CON of U.S. application Ser. No. 14/451,263 filed on Aug. 4, 2014, now U.S. Pat. No. 9,074,263, which is a DIV of U.S. application Ser. No. 14/041,970 filed on Sep. 30, 2013, now U.S. Pat. No. 8,835,114, which is a CON of U.S. application Ser. No. 14/040,399 filed on Sep. 27, 2013, now U.S. Pat. No. 8,785,125, which is a CON of U.S. application Ser. No. 13/678,402 filed on Nov. 15, 2012, now U.S. Pat. No. 8,574,841, which is a CON of U.S. application Ser. No. 13/216,107 filed on Aug. 23, 2011, now U.S. Pat. No. 8,334,098, which is a CON of U.S. application Ser. No. 12/643,934 filed on Dec. 21, 2009, now U.S. Pat. No. 8,026,066, which is a CON of U.S. application Ser. No. 11/926,984 filed on Oct. 29, 2007, now U.S. Pat. No. 7,682,792, which is a CON of U.S. application Ser. No. 11/296,931 filed on Dec. 8, 2005, now U.S. Pat. No. 7,354,719, which claims benefit of priority to U.S. Provisional App. No. 60/634,458 filed on Dec. 8, 2004, each of which is incorporated herein by reference.

REFERENCE TO SEQUENCE LISTING

The instant application contains a Sequence Listing which has been submitted in ASCII format via EFS-Web and is hereby incorporated by reference in its entirety. Said ASCII Copy, created on Oct. 9, 2019, is named "GP175-17-CN12_ST25.txt" and is 13,826 bytes in size.

FIELD

This invention relates to diagnostic detection of infectious agents associated with a risk for developing cancer, and specifically relates to compositions and assays for detecting human papillomavirus (HPV) by using in vitro nucleic acid amplification and detection assays to detect nucleic acid sequences.

BACKGROUND

Human papillomaviruses (HPV) target epithelial tissues for infection and are etiological agents of a variety of cancers, predominantly squamous cell carcinomas and adenocarcinomas. HPV-associated cancers include those of the head and neck (larynx, oral cavity, oropharynx, tonsils, and esophagus), respiratory tissue, breast, skin, cervix, and anus. Although HPV infection is considered a necessary factor in development of some cancers, other factors may also affect carcinogenesis (Braakhuis et al., 2004, *J. Natl. Cancer Inst.* 96(13): 998-1006; Dahlstrand et al., 2004, *Anticancer Res.* 24(3b): 1829-35; Daling et al., 2004, *Cancer* 101(2): 270-80; Ha et al., 2004, *Crit. Rev. Oral Biol. Med.* 15(4): 188-96; Hafkamp et al., *Acta Otolaryngol.* 124(4): 520-6; Harwood et al., 2004, *Br. J. Dermatol.* 150(5):949-57; Rees et al., 2004, *Clin. Otolaryngol.* 29(4): 301-6; Widschwendter et al., 2004, *J. Clin. Virol.* 31(4):292-7).

At least 77 different types of HPV have been identified. Of those, HPV16 and HPV18 are frequently linked to a variety of HPV-associated cancers, but the risk level associated with a HPV type may vary with different forms of papilloma-associated cancers. The pathogenesis of human papillomaviruses in epithelia has been studied to elucidate the link of HPV infection to cancers. HPV infect basal layer cells of stratified epithelia where they become established as multi-copy episomes or integrated genomes, by which the viral DNA is replicated with cellular chromosomes (reviewed by Longworth et al., 2004, *Microbiol. Mot Biol. Rev.* 68(2): 362-72). At cell division, a daughter cell migrates away from the basal layer and undergoes differentiation in which HPV vegetative viral replication and late-gene expression are activated to produce progeny HPV. Although an infected individual's immune system may clear the HPV infection, usually within 1 to 2 years, infected basal cells may persist for decades. HPV infection may lead to chromosomal instability and aneuploidy that may favor HPV integration (Melsheimer et al., 2004, *Clin. Cancer Res.* 10(9):3059-63; Reidy et al., 2004, *Laryngoscope* 114(11): 1906-9). During HPV genome integration, the HPV E2 gene may be destroyed, resulting in deregulated expression of the HPV E6/E7 oncogenes that encode oncoproteins that target the regulatory proteins pRb and p53. Thus, a cascade of events that modulate cellular regulation may result in carcinogenesis (Braun et al., 2004, *Cancer Lett.* 209(1):37-49; Fan et al., 2004, *Crit. Rev. Eukaryot. Gene Expr.* 14(3):183-202; Fiedler et al., 2004, *FASEB J.* 18(10):1120-2; Psyrri et al., 2004, *Cancer Res.*, 64(9):3079-86; Si et al., 2004, *J. Clin. Virol.* 32(1):19-23).

The association of HPV infection and cervical cancer has been the subject of considerable research and epidemiological study because of the high incidence of cervical cancer worldwide, estimated at 450,000 new cases per year. HPV types associated with a high risk of developing cervical cancer (HR-HPV) include HPV types 16, 18, 31, 33, 35, 39, 45, 51, 52, 56, 58, 59, 66, 68 and 73, although the epidemiological significance of individual types may vary with different geographical regions or clinical testing parameters (Munoz et al., 2004, *Int. J. Cancer* 111(2): 278-85; Chaturvedi et al., 2005, *J. Med. Virol.* 75(1):105-13; Smith et al., 2004, *Int. J. Gynaecol. Obstet.* 87(2):131-7). HPV infections that are generally considered a low risk for developing into cervical cancer (LR-HPV) include HPV types 6, 11, 43, 43, 44, 61, 71, and 72.

In women infected with HPV, cervical infection may lead to condylomata (genital warts), cervical intraepithelial neoplasia (CIN), and cervical cancer (Kahn et al., 2004, *Adolesc. Med. Clin.* 15(2): 301-21, ix). Cytological examination of cervical cells has been the primary screening tool for detecting cervical cancer in many countries, usually using the CIN grading system (1 to 3) to monitor precancerous lesions for determining treatment and/or further monitoring. In addition to cytological screening, molecular screening for HPV nucleic acid may be a cost-effective prognostic test that may allow extending the time interval between cytological tests (Wiley et al., 2004, *Curr. Oncol. Rep.* 6(6): 497-506; Zielinski et al., 2004, *Obstet. Gynecol. Surv.* 59(7): 543-53; Clavel et al., 2004, *Br. J. Cancer* 90(9):1803-8). Molecular assays have been developed for detection of selected HPV proteins and nucleic acid sequences in human biological specimens, e.g., Pap smears and biopsies (Chen et al., 2005, *Gynecol. Oncol.* 99(3):578-84; Carozzi et al., 2005, *Am. J. Clin. Pathol.* 124(5): 716-21; Molden et al., 2005, *Cancer Epidemiol. Biomarkers Prev.* 14(2): 367-72; Asato et al., 2004, *J. Infect. Dis.* 189(1):1829-32; Federschneider et al., 2004, *Am. J. Obstet. Gynecol.* 191(3): 757-61; Remmerbach et al., *J. Clin. Virol.* 30(4):302-8).

Vaccination against common HPV types may be useful to treat or prevent genital warts, condylomata, or prevent development of cancers, particularly cervical cancers. Various forms of HPV vaccinations are in development or testing (Ault et al., 2004, *Vaccine* 22(23-24):3004-7; Corona Gutierrez et al., 2004, *Hum. Genet. Ther.* 15(5):421-31; Harper et al., 2004, *Lancet* 364(9447):1757-65; Roden et al., 2004, *Hum. Pathol.* 35(8):971-82).

There is a need to efficiently and sensitively detect the presence of HPV in biological specimens to provide diagnostic and prognostic information to physicians treating patients infected with HPV, particularly for women whose cervical tissue has been infected with HR-HPV types. There is also a need to efficiently and sensitively detect the presence of HPV in biological specimens obtained from individuals who have been vaccinated against HPV infection, to determine the short-term and long-term efficacy of the vaccination.

SUMMARY

This invention includes compositions and methods for detection of nucleic acid sequences in multiple HPV types that may be present in a biological sample.

According to one aspect of the invention, there is provided a mixture of amplification oligomers in which individual oligomer sequences are selected from the group consisting of SEQ ID NO:18 to SEQ ID NO:42, which includes the complementary oligomer sequences or RNA equivalents of the specified sequences. A preferred embodiment of the mixture includes first amplification oligomers of SEQ ID Nos. 19 or 42, 21, 23, 25, 27, 29, 31, 33 and 35, and second amplification oligomers of SEQ ID Nos. 37, 38, 39, 40 and 41, or complementary oligomer sequences or RNA equivalents of the oligomer sequences. Another preferred embodiment includes first amplification oligomers of SEQ ID Nos. 18, 20, 22, 24, 26, 28, 30, 32, 34 and 36, and second amplification oligomers of SEQ ID Nos. 37, 38, 39, 40 and 41, or complementary oligomer sequences or RNA equivalents of the oligomer sequences. Another preferred embodiment includes first amplification oligomers of SEQ ID Nos. 19 or 42, 21, 23, 25, 27, 29, 31, 33 and 35, and second amplification oligomers of SEQ ID Nos. 38, 39, 40 and 41, or complementary oligomer sequences or RNA equivalents of the oligomer sequences. Another preferred embodiment includes first amplification oligomers of SEQ ID Nos. 18, 20, 22, 24, 26, 28, 30, 32, 34 and 36, and second amplification oligomers of SEQ ID Nos. 38, 39, 40 and 41, or complementary oligomer sequences or RNA equivalents of the oligomer sequences. In some embodiments of the mixture of oligomers, one or more individual oligomers include a backbone that includes at least one 2'-methoxy RNA group, at least one 2' fluoro-substituted RNA group, at least one peptide nucleic acid linkage, at least one phosphorothioate linkage, at least one methylphosphonate linkage, or any combination thereof. Embodiments of the mixtures may be contained in a kit.

According to another aspect of the invention, there is provided a mixture of oligomers in which individual oligomer sequences are selected from the group consisting of SEQ ID NO:11 to SEQ ID NO:17, SEQ ID NO:44 to SEQ ID NO:54 and SEQ ID NO:58, which includes the complementary oligomer sequences or RNA equivalents of the specified sequences. A preferred embodiment of the mixture includes SEQ ID Nos. 11 to 17, or complementary oligomer sequences or RNA equivalents of the oligomer sequences. Another preferred embodiment includes SEQ ID Nos. 11 to 15 and 17, or complementary oligomer sequences or RNA equivalents of the oligomer sequences. Another preferred embodiment includes SEQ ID Nos. 11 to 15 and 17 and at least one oligomer of SEQ ID NO:44 to SEQ ID NO:54 and SEQ ID NO:58, or complementary oligomer sequences or RNA equivalents of the oligomer sequences. Another preferred embodiment includes SEQ ID Nos. 11, 12, 14, 15, 17, 44, 45 and 52, or complementary oligomer sequences or RNA equivalents of the oligomer sequences. Preferred embodiments of the mixture include those in which each oligomer sequence includes a label joined directly or indirectly to the oligomer. In some preferred embodiments, each oligomer sequence includes a label that is a chemiluminescent compound, which is more preferably an acridinium ester (AE) compound. In some preferred embodiments of the mixture, each oligomer sequence has a backbone comprising at least one 2'-methoxy RNA group. Embodiments of these mixtures may be contained in a kit.

According to another aspect of the invention, there is provided a mixture of at least two oligomers in which individual oligomer sequences are selected from the group consisting of SEQ ID Nos. 1 to 10, which includes the complementary oligomer sequences or RNA equivalents of the specified sequences. A preferred embodiment of the mixture includes at least two oligomers selected from SEQ ID Nos. 2, 4, 6, 8 and 10 with a ligand moiety joined to each oligomer. Another preferred embodiment includes a mixture of oligomers of SEQ ID Nos. 2, 4, 6, 8 and 10 with a ligand moiety joined to each oligomer. Another preferred embodiment of the mixture includes at least two oligomers selected from SEQ ID Nos. 1, 3, 5, 7 and 9. Another preferred embodiment of the mixture includes oligomers of SEQ ID Nos. 1, 3, 5, 7 and 9. In some preferred embodiments, at least one oligomer has a backbone that includes at least one 2'-methoxy RNA group, at least one 2' fluoro-substituted RNA group, at least one peptide nucleic acid linkage, at least one phosphorothioate linkage, or at least one methylphosphonate linkage. Preferred embodiments of the mixtures are contained in a kit.

According to another aspect of the invention, there is provided a method of detecting human papillomavirus (HPV) nucleic acid present in a biological sample that includes the steps of:

contacting nucleic acid in a biological sample containing RNA of at least one of HPV types 16, 18, 31, 33, 35, 39, 45, 51, 52, 56, 58, 59 and 68 with a mixture of amplification oligomers that amplify a HPV sequence in an E6/E7 target region sequence, in which the mixture is made up of first amplification oligomers and second amplification oligomers for amplifying the HPV target region sequences of the multiple types; amplifying a HPV sequence from the target region sequence in at least one HPV type by using the amplification oligomers and a nucleic acid polymerase in vitro to produce an HPV amplified product; and detecting the amplified product by using a detection probe oligomer that is sufficiently complementary to hybridize specifically with the HPV amplified product to indicate the presence in the sample of at least one of HPV types 16, 18, 31, 33, 35, 39, 45, 51, 52, 56, 58, 59 and 68. In a preferred embodiment, the amplifying step uses first amplification oligomers of SEQ ID Nos. 19 or 42, 21, 23, 25, 27, 29, 31, 33 and 35, and second amplification oligomers of SEQ ID Nos. 37, 38, 39, 40 and 41, or complementary oligomer sequences or RNA equivalents of the oligomer sequences. Another preferred embodiment in the amplifying step uses first amplification oligomers of SEQ ID Nos. 18, 20, 22, 24, 26, 28, 30, 32, 34 and 36, and second amplification oligomers of SEQ ID Nos.

37, 38, 39, 40 and 41, or complementary oligomer sequences or RNA equivalents of the oligomer sequences. One preferred embodiment in the amplifying step uses first amplification oligomers of SEQ ID Nos. 19 or 42, 21, 23, 25, 27, 29, 31, 33 and 35, and second amplification oligomers of SEQ ID Nos. 38, 39, 40 and 41, or complementary oligomer sequences or RNA equivalents of the oligomer sequences. Another preferred embodiment in the amplifying step uses first amplification oligomers of SEQ ID Nos. 18, 20, 22, 24, 26, 28, 30, 32, 34 and 36, and second amplification oligomers of SEQ ID Nos. 38, 39, 40 and 41, or complementary oligomer sequences or RNA equivalents of the oligomer sequences. A preferred embodiment of the method further includes a step of separating RNA of at least one of HPV types 16, 18, 31, 33, 35, 39, 45, 51, 52, 56, 58, 59 and 68 from other components in the sample by contacting HPV RNA in the sample with a capture oligomer and separating a complex that includes the capture oligomer and HPV RNA from other components in the sample before the amplifying step. In a preferred embodiment that includes the separating step, the capture oligomer is present in a mixture of capture oligomers made up of at least two oligomers in which individual oligomer sequences are selected from the group consisting of SEQ ID Nos. 1 to 10, which includes the complementary oligomer sequences or RNA equivalents of the specified sequences. In preferred embodiments of the method that include the separating step, the capture oligomer is present in a mixture of capture oligomers made up of at least two oligomers selected from SEQ ID Nos. 2, 4, 6, 8 and 10 with a ligand moiety joined to each oligomer; or oligomers of SEQ ID Nos. 2, 4, 6, 8 and 10 with a ligand moiety joined to each oligomer; or at least two oligomers selected from SEQ ID Nos. 1, 3, 5, 7 and 9; or oligomers of SEQ ID Nos. 1, 3, 5, 7 and 9. In a preferred embodiment of the method, the amplifying step uses an amplification process that is substantially isothermal. A preferred embodiment of the method uses a transcription-associated amplification method in the amplifying step. One embodiment of the method in the detecting step uses a mixture of probe oligomers in which at least one probe oligomer binds specifically to the HPV amplified product and results in a signal to indicate the presence in the sample of at least one of the HPV types. In a preferred embodiment, the detecting step uses a mixture of probe oligomers made up of SEQ ID Nos. 11 to 17, or complementary oligomer sequences or RNA equivalents of the oligomer sequences. Another preferred embodiment in the detecting step uses a mixture of probe oligomers made up of SEQ ID Nos. 11 to 15 and 17, or complementary oligomer sequences or RNA equivalents of the oligomer sequences. Another preferred embodiment in the detecting step uses a mixture of probe oligomers made up of SEQ ID Nos. 11 to 15 and 17 and at least one oligomer of SEQ ID NO:44 to SEQ ID NO:54 and SEQ ID NO:58, or complementary oligomer sequences or RNA equivalents of the oligomer sequences. Another preferred embodiment in the detecting step uses a mixture of probe oligomers made up of SEQ ID Nos. 11, 12, 14, 15, 17, 44, 45 and 52, or complementary oligomer sequences or RNA equivalents of the oligomer sequences. One embodiment of the method further amplifies and detects a non-HPV internal control sequence. In a preferred embodiment that includes an internal control, the contacting step further includes introducing a non-HPV internal control sequence into the sample, the amplifying step further includes amplifying the non-HPV internal control sequence to produce an amplified internal control sequence, and the detecting step further includes detecting the amplified internal control sequence to produce a signal that indicates that the method steps have been performed appropriately.

The following description and accompanying drawing, which is part of the specification, serve to explain and illustrate the principles of the invention.

BRIEF DESCRIPTION OF THE DRAWINGS

FIG. 1 is a drawing of a phylogenetic tree showing the genetic relatedness of some HPV types.

DETAILED DESCRIPTION

This invention includes oligomer sequences and methods for detecting nucleic acid sequences from multiple HPV types (16, 18, 31, 33, 35, 39, 45, 51, 52, 56, 58, 59, 66, and 68) present in biological samples derived from humans. These sequences and methods are useful for diagnosis of HPV infections, including persistent infections for which detection of HPV sequences provides prognostic information related to carcinogenesis. The sequences and assays are also useful for monitoring the status of a patient at risk for cancer, and/or for assessing and monitoring a patient's response to a therapeutic treatment. Because the assays sensitively detect the presence of HPV nucleic acids, they are also useful for detecting vascular space invasion or lymph node metastases of HPV-associated cancers, thus providing further prognostic information. The sequences and assays are also useful for monitoring the efficacy of anti-HPV vaccination in individuals exposed to HPV after vaccination.

The targeted HPV types cumulatively represent high-risk types associated with cervical cancer. The oligomer sequences were designed to preferably detect more than one HPV type within the group by targeting E6/E7 gene sequences that are common or very similar between different HPV types, while avoiding adverse interactions between oligonucleotides that may occur when they are present in a mixture, such as an in vitro nucleic acid amplification reaction or a hybridization detection reaction. The sequences were also designed to avoid detecting related sequences found in HPV types that are characterized as low-risk for cervical cancer (e.g., HPV types 6, 11, 42, 43 and 44). Different HPV types were grouped based on their genetic relatedness, as shown in FIG. 1, for comparisons of target sequences, and are referred to herein as group A1 that includes HPV types 16, 31, and 35, group A2 that includes HPV types 33, 52, and 58, group B that includes HPV types 6, 11, 42, 43 and 44, group C1 that includes HPV types 18, 45, and 59, and group D that includes HPV types 51, 56 and 66. For comparison of sequences, known sequences obtained from a publicly available database (GenBank) were aligned either manually or by using a computerized algorithm and oligonucleotide sequences were selected for synthesis and testing by using the aligned sequences to suggest likely oligomers that fit a variety of criteria, including sequence length in a range of about 15 to 30 nt, GC content, and predicted Tm of a hybridization complex that includes the selected sequence, and a substantial lack of predictable secondary structure due to self-hybridization or intermolecular hybridization with other selected oligomers. Selected sequences were designed to specifically recognize the target HPV genomic or RNA sequence of one, or preferably more than one, HPV type within a group under substantially the same hybridization conditions for all of the selected oligonucleotide sequences. Known sequences used in alignments and selections included GenBank accession numbers AF092932, AF125673, AF404678, D90400, J04353, K02718, M12732, M27022, M73236, M14119, M62849, M74117, X05015, X74477, X74479, X74481, X74483, X77858, and Y13218. From the selected sequences, oligomers were synthesized in vitro using standard methods, and the synthetic oligomers were characterized, e.g., by experimentally determining $T_m$ of a hybridization complex that includes the oligomer and usually a synthetic RNA sequence that contains the complement of the oligomer sequence, and for their functional characteristics in nucleic acid amplification and detection reactions using conditions previously described in detail (e.g., U.S. Pat. Nos. 5,399,491 and 5,554,516, Kacian et al., and U.S. Pat. No. 5,283,174, Arnold et al.). For use in such methods, the HPV-specific sequences may be joined to additional sequences, e.g., with a 5' promoter sequence as shown in SEQ ID Nos. 18, 20, 22, 24, 26, 28, 30, 32, 34 and 36, or with a 3' tail sequence as shown in SEQ ID Nos. 1, 3, 5, 7 and 9.

To select oligomers efficiently that functioned in an assay to detect many different HPV types, the following process was used. First, oligomers to serve as detection probes for the HPV groups were selected, which determined the target area of the HPV genomic or RNA sequences to be amplified. Then, amplification oligomers were selected for each of the candidate target regions, synthesized, and tested in amplification reactions with individual HPV types of a group to be detected (e.g., HPV 16, 31 and 35 in group A1). If amplification and detection reactions produced substantially similar positive results for each HPV type in a group, then the oligomers for different groups (e.g., A1 and A2) were combined in multiplex amplification and detection reactions and tested for each of the HPV types in the combined groups to determine if the oligomer mixture functioned properly to provide positive results for each of the HPV types in the combined groups, or whether adverse interactions (e.g., between oligomers in the mixture) resulted in decreased assay sensitivity or specificity. If assay results in the multiplex format were unacceptable, one or more oligomers were redesigned, synthesized and tested in substantially the same manner. This process was reiterated for various combinations of oligomers to obtain combinations of oligomers that functioned in a multiplex assay to amplify and detect HPV types 16, 18, 31, 33, 35, 39, 45, 51, 52, 56, 58, 59, 66, and 68. Further optimization of the multiplex assay was achieved by using empirically determined optimal amounts of the oligomers in a mixture to produce positive results for each of the target HPV sequences while minimizing interfering interactions between the oligomers.

Selected oligomer sequences used to amplify and detect the multiple HPV types' sequences are summarized in Table 1. The HPV group designations for the sequences provided for convenience and it will be understood that an oligomer sequence may also functionally recognize HPV sequences of a type in another group in a multiplex reaction. Sequences in Table 1 are shown as DNA sequences, but it will be understood that these embodiments also encompass sequences consisting of their corresponding RNA sequences, and sequences that are completely complementary to the disclosed DNA sequences or their corresponding RNA sequences.

TABLE 1

| SEQ NO: | Group | Sequence |
|---|---|---|
| 1 | A1 | gctcataacagtggaggtcagttgcctctttaaaaaaa aaaaaaaaaaaaaaaaaaaaaaaa |
| 2 | A1 | gctcataacagtggaggtcagttgcctc |
| 3 | A2 | ctccaacacgctgcacagcgccctgtttaaaaaaaaaa aaaaaaaaaaaaaaaaaaaa |
| 4 | A2 | ctccaacacgctgcacagcgcctg |
| 5 | C1 | gtgcacagatcaggtagcttgtagggtcgtttaaaaaa aaaaaaaaaaaaaaaaaaaaaaaa |
| 6 | C1 | gtgcacagatcaggtagcttgtagggtcg |
| 7 | C2 | gcacaggtctggcaatttgtatggccgtttaaaaaaaa aaaaaaaaaaaaaaaaaaaaa |
| 8 | C2 | gcacaggtctggcaatttgtatggccg |
| 9 | D | ggtctttgacatctgtgacaccttattttaaaaaaaaa aaaaaaaaaaaaaaaaaaa |
| 10 | D | ggtctttgacatctgtgacaccttat |
| 11 | A1 | cagctggacaagcagaaccggac |
| 12 | A2 | ggccagatggacaagcacaac |
| 13 | C1 | tgtgtgtgtgttgtaagtgt |
| 14 | C2 | ccgaccatgcagttaatcacc |
| 15 | D | gcgtgaccagctaccagaaag |
| 16 | D | gccacagcaagctagacaagc |
| 17 | D | cacgtaccttgttgtgagtg |
| 18 | A1 | aatttaatacgactcactatagggagagaagcgtagag tcacacttgcaac |
| 19 | A1 | agcgtagagtcacacttgcaac |
| 42 | A1 | gaagcgtagagtcacacttgcaac |
| 20 | A1 | aatttaatacgactcactatagggagacacacaaacga agtgtagacttacactgac |
| 21 | A1 | cacacaaacgaagtgtagacttacactgac |
| 22 | A1 | aatttaatacgactcactatagggagagtgtcgcctca catttacaacaggacg |
| 23 | A1 | gtgtcgcctcacatttacaacaggacg |
| 24 | A2 | aatttaatacgactcactatagggagagttacaatgta gtaatcagctgtggc |
| 25 | A2 | gttacaatgtagtaatcagctgtggc |
| 26 | A2 | aatttaatacgactcactatagggagacacaatgtagt aattacttgtggc |
| 27 | A2 | cacaatgtagtaattacttgtggc |
| 28 | C1 | aatttaatacgactcactatagggagagcacaccacgg acacacaaagga |
| 29 | C1 | gcacaccacggacacacaaagga |
| 30 | C1 | aatttaatacgactcactatagggagaggatagtgtgt ccataaacagctgctg |
| 31 | C1 | ggatagtgtgtccataaacagctgctg |

TABLE 1-continued

| SEQ NO: | Group | Sequence |
|---|---|---|
| 32 | C2 | aatttaatacgactcactatagggagaccgtctggcta gtagttgatg |
| 33 | C2 | ccgtctggctagtagttgatg |
| 34 | D | aatttaatacgactcactatagggagaccactgccagt tgtactacacttgaac |
| 35 | D | ccactgccagttgtactacacttgaac |
| 36 | D | aatttaatacgactcactatagggagactctgaatgtc caactgcaccacaaac |
| 37 | D | ctctgaatgtccaactgcaccacaaac |
| 38 | A1, A2 | gtgacagctcagatgaggatg |
| 39 | C1 | cgacgagccgaaccac |
| 40 | C2 | gaccttgtatgtcacgagc |
| 41 | D | gacagctcagaggaggaggatg |
| 44 | C1 | gtagtagaaagctcagcagacgacc |
| 45 | C1 | gtagagagctcggcagaggac |
| 46 | C1 | gtagagagctcggcagaigac (wherein "i" is inosine) |
| 47 | C1 | gaccttagaacactacagcagc |
| 48 | C1 | gtgtgacggcagaattgagc |
| 49 | C1 | cttcagctagtagtagaaacctcgc |
| 50 | C1 | cagctagtagtagaaacctcgcaagac |
| 51 | C1 | agctagtagtagaaacctcgcaagacgg |
| 52 | C1 | gtagtagaaacctcgcaagacgg |
| 53 | C1 | gtagaaacctcgcaagacgg |
| 54 | C1 | gcaagacggattgcgagcct |
| 58 | D | gagcaatttgacagctcagagg |

As described below, some of these oligomers are preferably used as amplification oligomers which include embodiments referred to as promoter primers, some are preferably used as detection probes, and some are preferably used as capture probe oligomers to facilitate separation of HPV nucleic acid from other components of a biological sample before amplification of the HPV target sequence. Capture probe oligomers preferably target sequences in E6/E7 gene sequences, whereas amplification and detection oligomers preferably target E7 gene sequences. These oligomer sequences and methods that use them are useful for detecting many different HPV types that are associated with an increased risk of developing cancer in humans. They are useful for detecting expression of HPV genes E6 and E7, which, when constitutively expressed in human cells, lead to cell cycle deregulation and cell proliferation that may progress to cancer. Because HPV E6/E7 gene expression is suppressed in cells that harbor episomal HPV, the assay and oligomer components was designed to detect E6/E7 RNA present in a biological sample to provide prognostic information by detecting HPV expression associated with neoplasia and carcinogenesis.

To aid in understanding the invention and its preferred embodiments, the following definitions are provided. Other scientific and technical terms used herein have the same meaning as commonly understood by those skilled in the relevant art. General definitions of terms may be found in, e.g., *Dictionary of Microbiology and Molecular Biology*, 2nd ed. (Singleton et al., 1994, John Wiley & Sons, New York, N.Y.) or *The Harper Collins Dictionary of Biology* (Hale & Marham, 1991, Harper Perennial, New York, N.Y.). Unless otherwise described, the techniques employed or contemplated herein are standard methodologies that are well known to one of ordinary skill in the art.

A "biological sample" refers to any tissue or material derived from a living or dead human which may contain the target nucleic acid, including, for example, samples of larynx, oral cavity, oropharynx, tonsil, or esophagus tissue, respiratory tissue or exudates, cervical or anal swab samples, biopsy tissue including lymph nodes, gastrointestinal tissue, feces, urine, semen, sputum, peripheral blood, plasma, serum or other body fluids, tissues or materials. A biological sample may be treated to physically or mechanically disrupt tissue or cell structure to release intracellular components into a solution which may further contain enzymes, buffers, salts, detergents and the like, using well known methods.

"Nucleic acid" refers to a multimeric compound (oligomer or polymer) comprising nucleosides or nucleoside analogs which have nitrogenous bases, or base analogs, and which are linked together by phosphodiester bonds or other known linkages to form a polynucleotide. Nucleic acids include conventional ribonucleic acid (RNA), deoxyribonucleic acid (DNA), or chimeric DNA-RNA, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305, Hydig-Hielsen et al.), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine; *The Biochemistry of the Nucleic Acids* 5-36, Adams et al., ed., 11$^{th}$ ed., 1992), derivatives of purine or pyrimidine bases (e.g., N$^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines, and pyrazolo-compounds, such as unsubstituted or 3-substituted pyrazolo[3, 4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481, Arnold et al.). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids also include "locked nucleic acids" (LNA), an analogue containing one or more LNA nucleotide monomers with a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, *Biochemistry*

43(42):13233-41). Synthetic methods for making nucleic acids in vitro are well known in the art.

The interchangeable terms "oligomer" and "oligonucleotide" refer to a nucleic acid having generally less than 1,000 residues, including those in a size range having a lower limit of about 2 to 5 nucleotides. Preferred oligomers fall in a size range having a lower limit of about 5 to about 15 nucleotides and an upper limit of about 60 to 150 nucleotides. More preferably, oligomers are in a size range of about 15 to 100 nucleotides. Oligomers may be purified from naturally occurring sources, but preferably are synthesized by using any known enzymatic or chemical methods.

An "amplification oligonucleotide" or "amplification oligomer" refers to an oligomer that hybridizes to a target nucleic acid, or its complement, and participates in an in vitro nucleic acid amplification reaction. An amplification oligomer may be referred to as a "primer" or "promoter primer." Generally, a primer hybridizes to a template nucleic acid strand and has a 3' end that is extended in a polymerization reaction to produce a complementary strand to the template strand. The 5' region of a primer may be non-complementary to the target nucleic acid, e.g., it may contain a 5' promoter sequence and the oligomer is referred to as a promoter primer. Those skilled in the art will appreciate that any oligomer that has a target-complementary sequence and functions as a primer can be modified to include a 5' promoter sequence, and thus function promoter primer. Similarly, a promoter primer can function as a primer independent of its promoter sequence. Preferred embodiments of amplification oligonucleotides contain at least 10 contiguous bases, and more preferably at least 12 contiguous bases, that are complementary to a target sequence (or a complementary strand thereof). The contiguous bases are preferably at least about 80%, more preferably at least about 90%, and most preferably about 100% complementary to the target region to which the oligomer hybridizes. An amplification oligomer is preferably about 10 to about 65 nucleotides long and may include modified nucleotides or base analogs.

"Amplification" refers to an in vitro method for obtaining multiple copies of a target sequence, its complement, or fragments of a target sequence. Amplification of "fragments" refers to production of an amplified nucleic acid that contains less than the complete target region sequence or its complement. For example, a complete gene may be referred to as a target sequence for an assay, but amplification may make copies of a smaller sequence (e.g., about 85 to 200 nucleotides) contained in the target gene sequence. Known amplification methods include, e.g., transcription-associated amplification, replicase-mediated amplification, the polymerase chain reaction (PCR), ligase chain reaction (LCR), and strand-displacement amplification (SDA). Replicase-mediated amplification uses self-replicating RNA molecules, and a replicase such as QB-replicase (U.S. Pat. No. 4,786,600, Kramer et al.). PCR amplification uses DNA polymerase, primers and thermal cycling to synthesize multiple copies of two complementary strands of DNA or cDNA (U.S. Pat. Nos. 4,683,195, 4,683,202, and 4,800,159, Mullis et al., and *Methods in Enzymology*, 1987, Vol. 155: 335-350). LCR amplification uses at least four separate oligonucleotides to amplify a target and its complementary strand by using multiple cycles of hybridization, ligation, and denaturation (e.g., U.S. Pat. No. 5,427,930, Birkenmeyer et al., U.S. Pat. No. 5,516,663, Backman et al., and EP Pat. App. No. 0 320 308). SDA uses a primer that contains a recognition site for a restriction endonuclease such that the endonuclease will nick one strand of a hemimodified DNA duplex that includes the target sequence, followed by amplification in a series of primer extension and strand displacement steps (e.g., U.S. Pat. No. 5,422,252, Walker et al., U.S. Pat. No. 5,547,861, Nadeau et al., U.S. Pat. No. 5,648,211, Fraiser et al.). Transcription-associated amplification is a preferred embodiment described below. It will be apparent to one skilled in the art that the oligonucleotides and methods illustrated by the preferred embodiments may be readily adapted to use in any primer-dependent amplification system by one skilled in the art of molecular biology.

"Transcription-associated amplification" or "transcription-mediated amplification" (TMA) refer to any type of nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. Variations of transcription-associated amplification are well known in the art as disclosed in detail previously (U.S. Pat. Nos. 5,399,491 and 5,554,516, Kacian et al.; U.S. Pat. No. 5,437,990, Burg et al.; PCT Nos. WO 88/01302 and WO 88/10315, Gingeras et al.; U.S. Pat. No. 5,130,238, Malek et al.; U.S. Pat. Nos. 4,868,105 and 5,124,246, Urdea et al.; PCT No. WO 95/03430, Ryder et al.; and U.S. patent application Ser. No. 11/213,519, Becker et al., filed Aug. 26, 2005). The TMA methods of Kacian et al. are preferred embodiments of amplification methods used for detection of target sequences as described below. Although preferred embodiments are illustrated by using TMA or transcription-associated amplification, a person of ordinary skill in the art will appreciated that amplification oligomers disclosed herein may be readily applicable to use in other amplification methods based on polymerase-mediated extension of oligomer sequences.

A "detection probe" refers to a nucleic acid oligomer that hybridizes specifically to a target sequence in a nucleic acid, preferably in an amplified sequence, under conditions that promote hybridization, to allow detection of the target sequence or amplified nucleic acid. Detection may either be direct (i.e., resulting from a probe hybridizing directly to the target or amplified nucleic acid) or indirect (i.e., resulting from a probe hybridizing to an intermediate molecular structure that links the probe to the target or amplified nucleic acid). A probe's "target" generally refers to a sequence within (i.e., a subset of) an amplified nucleic acid sequence which hybridizes specifically to at least a portion of a probe oligomer using standard hydrogen bonding (base pairing), although a probe sequence does not have to be 100% complementary to the target sequence. Sequences that are "sufficiently complementary" allow stable hybridization of a probe oligomer to a target sequence that is not completely complementary to the probe's target-specific sequence. In addition to its target-specific sequences, a probe may include other sequences that contribute to its three-dimensional conformation or detection function (e.g., U.S. Pat. Nos. 5,118,801 and 5,312,728, Lizardi et al.; U.S. Pat. Nos. 6,849,412, 6,835,542, 6,534,274, and 6,361,945, Becker et al.).

By "sufficiently complementary" is meant a contiguous nucleic acid sequence that is capable of hybridizing to another sequence by hydrogen bonding between a series of complementary bases, which may be complementary at each position in the sequence by using standard base pairing (e.g., G:C, A:T or A:U pairing) or may contain one or more non-complementary residues so long as the entire sequence is capable of specifically hybridizing with another sequence in appropriate hybridization conditions. Contiguous bases are preferably at least about 80%, more preferably at least about 90%, and most preferably about 100% complementary to a sequence to which an oligomer is intended to specifically hybridize. Appropriate hybridization conditions are well known to those skilled in the art, can be predicted readily based on sequence composition, or can be determined empirically by using routine testing (e.g., Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57 particularly at §§ 9.50-9.51, 11.12-11.13, 11.45-11.47 and 11.55-11.57).

A "capture probe" or "capture oligomer" refers to at least one nucleic acid oligomer that provides a means for specifically joining a target sequence to a support to separate the target nucleic acid from other components in a mixture. A capture oligomer may rely on any known ligand interaction to link the target to a support, and preferred embodiments link the target to an immobilized oligomer on a support by using base pair hybridization. Embodiments of capture oligomers may include two binding regions: a target sequence-binding region and an immobilized probe-binding region, usually on the same oligomer, although the regions may be present on two different oligomers joined together by one or more linkers. An "immobilized probe" refers to a nucleic acid that joins, directly or indirectly, a capture oligomer to an immobilized support. An immobilized oligomer joined to a solid support facilitates separation of the bound target sequence from unbound material in the mixture. Any known solid support may be used, e.g., matrices or particles in solution, made of any known support material, e.g., nitrocellulose, nylon, glass, polyacrylate, mixed polymers, polystyrene, silane polypropylene and metal particles, preferably, magnetically attractable particles. Preferred target capture materials and methods have been previously described in detail (U.S. Pat. Nos. 6,110,678 and 6,280,952, Weisburg et al.).

By "separating" or "purifying" is meant that one or more components of a biological sample are removed from one or more other components of the sample. For example, sample components include nucleic acids in a generally aqueous solution that may include other materials such as proteins, carbohydrates, lipids and cellular organelles or debris. Preferably, a separating or purifying step removes at least about 70%, more preferably at least about 90% and, even more preferably, at least about 95% of the other components present in the sample from the desired target.

A "label" refers to a molecular moiety or compound that can be detected or can lead to a detectable response. A label can be joined directly or indirectly to a nucleic acid probe. Direct labeling can occur through bonds or interactions that link the label to the probe, including covalent bonds or non-covalent interactions, e.g., hydrogen bonding, hydrophobic and ionic interactions, or formation of chelates or coordination complexes. Indirect labeling can occur through use of a bridging moiety or "linker" which is/are either directly or indirectly labeled, and which may amplify a detectable signal. Labels can be any known detectable moiety, e.g. radionuclides, ligands, enzyme or enzyme substrate, reactive group, or chromophore, such as a dye, bead, or particle that imparts a detectable color, luminescent compounds (e.g., bioluminescent, phosphorescent or chemiluminescent labels) and fluorescent compounds. Preferably, the label on a labeled probe is detectable in a homogeneous assay system, i.e., bound labeled probe in a mixture containing unbound probe exhibits a detectable change, such as stability or differential degradation, compared to unbound probe. A preferred label for use in a homogenous assay is a chemiluminescent compound, and preferred chemiluminescent labels are acridinium ester ("AE") compounds, that include standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE) (U.S. Pat. No. 5,656,207, Woodhead et al.; U.S. Pat. No. 5,658,737, Nelson et al.; and U.S. Pat. No. 5,639,604, Arnold, Jr., et al.). Synthesis and methods of attaching labels to nucleic acids and detecting labels are well known (see Sambrook et al., *Molecular Cloning, A Laboratory Manual*, 2nd ed. (Cold Spring Harbor Laboratory Press, Cold Spring Harbor, N.Y., 1989), Chapter 10; U.S. Pat. No. 5,658,737, Nelson et al.; U.S. Pat. No. 5,656,207, Woodhead et al.; U.S. Pat. No. 5,547,842, Hogan et al.; U.S. Pat. No. 5,283,174, Arnold et al.; U.S. Pat. No. 4,581,333, Kourilsky et al.; and European Pat. App. Pub. No. 0 747 706, Becker et al.).

By "consisting essentially of" is meant that additional component(s), composition(s) or method step(s) that do not materially change the ability to detect the specified multiple HPV target sequences of any one or all of groups A1, A2, C1, C2, and D by using an in vitro amplification reaction using embodiments of the disclosed amplification oligomers and detection by using embodiments of the disclosed detection probes may be included in the compositions, kits, or methods of the present invention. Any component(s), composition(s), or method step(s) that interfere with the ability of these materials or procedures to detect the specified multiple HPV target sequences of any one of groups A1, A2, C1, C2, and D by using in vitro amplification and detection reactions would fall outside of this term.

The present invention includes compositions (nucleic acid capture oligomers, amplification oligomers and probes) and methods for detecting HPV nucleic acid in a human biological sample. To select oligomer sequences appropriate for use as capture probes, amplification oligomers, and detection probes, known HPV RNA or DNA sequences of 31 different known subtypes (including partial sequences) available from publicly accessible databases (e.g., GenBank) were aligned by matching regions of the same or similar sequences in the E6/E7 gene sequences and compared by using well known molecular biology techniques. Additional features considered in designing the oligomers included the relative GC content of the sequence, the relative absence of predicted secondary structure (e.g., hairpin turns forming intramolecular hybrids), the relative absence of predicted intermolecular interactions when the oligomers were present in a mixture under hybridization conditions, using methods well known in the art. Although such comparisons and predictions may be facilitated by the use of computerized algorithms, those skilled in the art can readily perform such comparisons manually. The HPV E6/E7 sequences were compared and sequences of closely related types with substantial sequence similarity were segregated into the groups A1, A2, B, C1, C2, and D. Sequence comparisons were made both within the closely related groups and between groups and portions of E6/E7 sequences that contained relatively few sequence variants within a group (i.e., consensus regions) were identified and chosen as a basis for designing synthetic oligomers suitable hybridization to target sequences in one or more HPV types. By designing oligomers for consensus sequences, instead of combinations of amplification and detection oligomers specific for each individual HPV type to be detected, the total number of oligomers in a reaction mixture is reduced, thus reducing the probability of unintended oligomer interactions that are known to occur in amplification reactions (e.g., formation of "primer dimers" or non-target amplification products), and also reducing background signals which are generally proportional to the number of detection probes used in a single reaction. Oligomers based on using consensus sequences, however, are generally more difficult to design because the target regions available for designing consensus sequences may be more limited and some of the designed oligomers may not be completely complementary to one or more of the intended target sequences. That is, for one or more of the HPV types to be detected by using these combinations of oligomers, one or more mismatches may occur between an oligomer sequence and its intended complementary target sequence for one or more of the HPV types in a group. Also, an oligomer may be a complete match to one HPV type's target sequence in a group (e.g., HPV16 in group A1) and contain mismatch(es) to other HPV types in the group (e.g., HPV 31 and/or 35), but still function in amplifying and/or detecting the types in the group. Similarly, an oligomer designed to function for one group (e.g., an amplification oligomer for group A2) may function in combination with other amplification oligomers to amplify sequences in multiple types of more than one group (e.g., types in groups A1 and A2). Based on these considerations, amplification oligomers were designed to hybridize to HPV gene sequences (sense strand or the complementary strand sequence) in the E7 gene, generally to amplify sequences of about 80 to about 150 nucleotides (e.g., embodiments amplified sequences of 107 nt for HPV16, 152 nt for HPV18, 118 nt for HPV31, 82 nt for HPV33, 109 nt for HPV35, 96 nt for HPV39, 152 nt for HPV45, 133 nt for HPV51, 86 nt for HPV52, 146 nt for HPV56, 83-85 nt for HPV58, 132 nt for HPV59, and 99 nt for HPV68). Detection probes were designed to hybridize to a target sequence contained within the amplified sequence made by using the corresponding set of primers, i.e., to detect a sequence between the target sequences of a particular set of primers. The target regions for designing capture probe oligomers generally were located in the E6/E7 gene sequences 5' to the target sequences for amplification of an HPV type or group. In many cases, reiterations of redesign and empirical testing were performed to optimize selection of the oligomers presented in Table 1.

Embodiments of capture probe oligomers include those of SEQ ID Nos. 1 to 10, with preferred embodiments including a substantially homopolymeric 3' tail region ($T_3A_{30}$), as shown in SEQ ID Nos. 1, 3, 5, 7, and 9.

Embodiments of detection probe oligomers include those of SEQ ID Nos. 11 to 17, 41, 44 to 54, and 58. From about 50 designs that were synthesized as oligomers and tested, preferred probe oligomers had a size range of 20 to 23 nt, a GC content in a range of about 40 to 50%, and an estimated melting temperature ($T_m$) in the range of about 55° C. to 70° C. Embodiments of probe oligomers were synthesized and labeled with an AE chemiluminescent compound (e.g., 2-methyl-AE) by using a non-nucleotide linker moiety and methods previously described in detail (U.S. Pat. Nos. 5,185,439, 5,585,481, and 5,656,744, Arnold Jr. et al., and U.S. Pat. No. 5,639,604, Arnold et al., see column 10, line 6 to column 11, line 3, and Example 8). Preferred labeling positions occur in a central region of an oligomer, near a region of A/T base pairs, at a 3' or 5' terminus, or at or near a mismatch site with a known non-target sequence to be avoided in detection. Embodiments of AE-labeled probes include those labeled at the following positions: between nt 4 and 5 for SEQ ID Nos. 15 and 53, between nt 5 and 6 for SEQ ID Nos. 11, 14, 17, 44, 50 and 52, between nt 7 and 8 for SEQ ID Nos.15, 17, 47, 48, 52 and 54, between nt 8 and 9 for SEQ ID Nos. 12, 14, 41, 45, 47, 49, 54 and 58, between nt 9 and 10 for SEQ ID Nos. 47 and 48, between nt 10 and 11 for SEQ ID Nos. 17, 44 and 47, between nt 11 and 12 for SEQ ID Nos. 13, 44, 45, 46, 47, 50, 51 and 53, between nt 12 and 13 for SEQ ID Nos. 13, 15, 51 and 53, between nt 13 and 14 for SEQ ID Nos. 14, 16, 45, 47 and 54, between nt 14 and 15 for SEQ ID Nos. 13, 14, 49 and 52, between nt 15 and 16 for SEQ ID Nos. 13 and 52, between nt 16 and 17 for SEQ ID NO:44, between nt 17 and 18 for SEQ ID Nos. 44, 47 and 58, between nt 19 and 20 for SEQ ID NO:51, between nt 20 and 21 for SEQ ID NO:50, and between nt 21 and 22 for SEQ ID NO:44. Preferred embodiments include AE-labeled probes labeled at the following positions: between nt 5 and 6 for SEQ ID NO:11, between nt 7 and 8 for SEQ ID Nos.15, and 17, between nt 8 and 9 for SEQ ID NO:12, between nt 10 and 11 for SEQ ID NO:44, between nt 11 and 12 for SEQ ID NO:45, between nt 13 and 14 for SEQ ID NO:14, and between nt 14 and 15 for SEQ ID NO:52. Preferred embodiments of detection probes were synthesized as sequences of RNA bases linked by 2' methoxy backbones. Probe embodiments of SEQ ID Nos. 49 to 54 cumulatively target the sequence of SEQ ID NO:55, and overlapping probes of SEQ ID Nos. 49 to 53 all include the sequence of SEQ ID NO:56.

Embodiments of these detection probes include mixtures of probes that detect HPV sequences in the multiple HPV types contained in groups A1, A2, C2, C2 and D, i.e., HPV types 16, 31, 35, 33, 52, 58, 18, 45, 59, 39, 68, 51 and 56. A preferred embodiment of such a mixture is made up of detection probes of SEQ ID Nos. 11 to 15 and 17. A particularly preferred embodiment is a mixture of AE-labeled probes of SEQ ID NO:11 labeled between nt 5 and 6, SEQ ID NO:12 labeled between nt 8 and 9, SEQ ID NO:13 labeled between nt 15 and 16, SEQ ID NO:14 labeled between nt 13 and 14, SEQ ID NO:15 labeled between nt 7 and 8, and SEQ ID NO:17 labeled between nt 7 and 8. Another preferred embodiment of such a mixture is made up of probes of SEQ ID Nos. 11, 12, 14, 15, 17, 44, 45 and 52. A particularly preferred embodiment is a mixture of AE-labeled probes of SEQ ID NO:11 labeled between nt 5 and 6, SEQ ID NO:12 labeled between nt 8 and 9, SEQ ID NO:14 labeled between nt 13 and 14, SEQ ID NO:15 labeled between nt 7 and 8, SEQ ID NO:17 labeled between nt 7 and 8, SEQ ID NO:44 labeled between nt 10 and 11, SEQ ID NO:45 labeled between nt 11 and 12, and SEQ ID NO:52 labeled between nt 14 and 15. Those skilled in the art will appreciate that detection probes may be used to detect HPV types of individual groups, e.g., HPV types in group A1, A2, C1, C2, or D, or combinations of related types, such as those in groups A1 and A2. Preferred embodiments of such detection probes identified by their respective target groups include those of SEQ ID NO:11 for group A1, SEQ ID NO:12 for group A2, SEQ ID NO:13 or a mixture of SEQ ID Nos. 44, 45 and 52 for group C1, SEQ ID NO:14 for group C2, and SEQ ID Nos. 15 and 17 for group D.

Embodiments of amplification oligomers include those of SEQ ID Nos. 18 to 42. Some embodiments contain only sequences that target HPV sequences, i.e., those of SEQ ID Nos. 19, 21, 23, 25, 27, 29, 31, 33, 35, 37, 38, 39, 40, 41, and 42, whereas others contain additional functional sequences, i.e., promoter sequences. Embodiments of promoter primers that include the promoter sequence of SEQ ID NO:43 at the 5' end of the oligomer includes those of SEQ ID Nos. 18, 20, 22, 24, 26, 28, 30, 32, 34, and 36. Sequences that are structurally related as HPV-specific sequences and promoter primers that include a 5' promoter sequence attached to the HPV-specific sequence are the following: SEQ ID Nos. 19 and 18, SEQ ID Nos. 42 and 18, SEQ ID Nos. 21 and 20, SEQ ID Nos. 23 and 22, SEQ ID Nos. 25 and 24, SEQ ID Nos. 27 and 26, SEQ ID Nos. 29 and 28, SEQ ID Nos. 31 and 30, SEQ ID Nos. 33 and 32, SEQ ID Nos. 35 and 34, and SEQ ID Nos. 37 and 36. Preferred mixtures or combinations of amplification oligomers for amplifying sequences of the HPV types by groups include those of: SEQ ID NO:18 or 19, SEQ ID NO:20 or 21, and SEQ ID NO:22 or 23, with SEQ ID NO:38 for group A1, SEQ ID NO:24 or 25, and SEQ ID NO:26 or 27, with SEQ ID NO:38 for group A2, SEQ ID NO:28 or 29, and SEQ ID NO:30 or 31, with SEQ ID NO:39 for group C1, SEQ ID NO:32 or 33 with SEQ ID NO:40 for group C2, and SEQ ID NO:34 or 35, and SEQ ID NO:36 or 37, with SEQ ID NO:41 for group D. Preferred embodiments use a mixture of amplification oligomers that together amplify sequences from HPV types 16, 31, 35, 33, 52, 58, 18, 45, 59, 39, 68, 51 and 56 (i.e., HPVs contained in all of groups A1, A2, C1, C2 and D). One preferred embodiment of such a mixture of amplification oligomers for HPV types 16, 31, 35, 33, 52, 58, 18, 45, 59, 39, 68, 51 and 56 include those of SEQ ID Nos. 18, 20, 22, 24, 26, 28, 30, 32, 34, 36, 38, 39, 40, and 41. Another preferred embodiment of such a mixture of amplification oligomers for HPV types 16, 31, 35, 33, 52, 58, 18, 45, 59, 39, 68, 51 and 56 include those of SEQ ID Nos.19, 21, 23, 25, 27, 29, 31, 33, 35, 37, 38, 39, 40, and 41.

The assay to detect multiple HPV sequences in a biological sample includes the steps of amplifying at least one HPV nucleic acid sequence of an E6/E7 target region from an HPV type contained in HPV group A1, A2, C1, C2, or D by using at least two amplification oligomers as primers to produce an amplified nucleic acid, preferably in a transcription-associated amplification reaction, and detecting the amplified nucleic acid by hybridizing it with a detection probe sequence that is sufficiently complementary to a sequence contained in the amplified nucleic acid. A preferred embodiment uses a mixture of amplification oligomers of SEQ ID Nos. 18, 20, 22, 24, 26, 28, 30, 32, 34, 36, 38, 39, 40, and 41 in the amplification reaction that is a transcription-associated amplification reaction. Another preferred embodiment uses a mixture of amplification oligomers of SEQ ID Nos. 19, 21, 23, 25, 27, 29, 31, 33, 35, 37, 38, 39, 40, and 41 in the amplification reaction. The amplified nucleic acid is detected by detecting a signal that results from binding the detection probe specifically to an amplified sequence, even though such specific binding may not result from hybridization of sequences in the amplified nucleic acid that are completely complementary to the detection probe sequence. Detecting a signal may result from instances in which the amplified sequence is unlabeled and is bound to a labeled detection probe, in which the bound labeled detection probe provides a detectable signal. Detecting a signal may result from instances in which the amplified nucleic acid is bound to an unlabeled probe, followed by detection of the complex that includes the amplified nucleic acid and the probe, such as by detecting a signal resulting from formation of the hybridization complex made up of the detection probe and the amplified nucleic acid, e.g., an electrical signal. Preferred embodiments use probes of SEQ ID Nos. 11 to 17, labeled with a chemiluminescent compound. Preferred embodiments use a mixture of detection probes that detect amplified HPV sequences of HPV types 16, 31, 35, 33, 52, 58, 18, 45, 59, 39, 68, 51 and 56. A preferred embodiment of a probe mixture used for detection is made up of probes of SEQ ID Nos. 11 to 15 and 17, more preferably labeled with a chemiluminescent label. Another preferred embodiment of a probe mixture used for detection is a mixture of AE-labeled probes of SEQ ID Nos.11 to 15 and 17. Another preferred embodiment of a probe mixture used for detection is made up of probes of SEQ ID Nos. 11, 12, 14, 15, 17, 44, 45 and 52, more preferably labeled with a chemiluminescent label. Another preferred embodiment of a probe mixture for detection is a mixture of AE-labeled probes of SEQ ID Nos. 11, 12, 14, 15, 17, 44, 45 and 52. Additional embodiments of the assay may use detection probes to detect HPV types of individual groups, such as in confirmatory assaying of the amplified nucleic acid sequences to detect HPV types in group A1, A2, C1, C2, or D, or combinations of HPV types, such as those in groups A1 and A2. Preferred embodiments of such assays use detection probes of SEQ ID NO:11 for detection of HPV types in group A1, SEQ ID NO:12 for detection of HPV types in group A2, SEQ ID NO:13 or a mixture of SEQ ID Nos. 44, 45 and 52 for detection of HPV types in group C1, SEQ ID NO:14 for detection of HPV types in group C2, or SEQ ID Nos. 15 and 17 for detection of HPV types in group D.

Another embodiment of the assay uses two amplification and detection reactions for each biological sample tested. The first reaction includes a mixture of amplification oligomers that can amplify the HPV types in groups A1, A2, C1, C2, or D, to produce at least one amplified HPV sequence from at least one of the HPV types. The second reaction includes a mixture of amplification oligomers to amplify sequences of both HPV types 16 and 18. The amplified products of the two amplification reactions then are detected separately. For the first amplification reaction, the amplified products are detected with a mixture of detection probes that detect HPV types of groups A1, A2, C1, C2, and D, to detect the presence of at least one of those HPV types in the sample. For the second amplification reaction, the amplified products are detected with a mixture of detection probes specific for detection of HPV 16 and HPV 18 amplified sequences, to detect the presence of HPV16, HPV18, or both types in the sample. This assay provides additional diagnostic information because when the first amplification and detection reactions provide a positive result, then the sample contained any one of the HPV types of groups A1, A2, C1, C2, and D. If the second amplification and detection reactions also provide a positive result, then the tested sample contained at least one of the most commonly found HR-HPV type(s), HPV 16 and/or HPV 18. If the first reaction provides a positive result and the second reaction provides a negative result, then a HR-HPV type is present in the sample, but it is not HPV16 or HPV 18. Based on such information, medical personnel may select the appropriate follow-up monitoring for such a patient. Embodiments of the assay use in the first reaction a mixture of amplification oligomers of SEQ ID Nos. 18, 20, 22, 24, 26, 28, 30, 32, 34, 36, 38, 39, 40, and 41, or a mixture of amplification oligomers of SEQ ID Nos. 19, 21, 23, 25, 27, 29, 31, 33, 35, 37, 38, 39, 40, and 41, and amplified products are detected with a mixture of probe oligomers of SEQ ID Nos. 11 to 15 and 17 or a mixture made up of probes of SEQ ID Nos. 11, 12, 14, 15, 17, 44, 45 and 52. In the second reaction for HPV16 and HPV18 detection, a mixture of amplification oligomers of SEQ ID Nos. 18, 28, and 39, or a mixture of amplification oligomers of SEQ ID Nos. 19, 29, and 39 are used in the amplifying step, and the detecting step uses a mixture of detection probes of SEQ ID Nos. 11 and 13. Another assay embodiment for a single sample includes three reactions: a first reaction to amplify and detect any one of the HPV types of groups A1, A2, C1, C2, and D as described above, a second reaction to amplify and detect specifically only HPV 16 sequences, and a third reaction to amplify and detect specifically only HPV 18 sequences. This three-part assay provides significant diagnostic information on the types of HPV nucleic acid present in the sample by using relatively few reactions.

The assays for HPV detection may also include a step of isolating or purifying a target HPV RNA before the amplification step by using a capturing step. Preferred embodiments use a mixture of capture probe oligomers under hybridizing conditions, one portion of a capture oligomer specifically hybridizes to an HPV E6/E7 target sequence of at least one HPV type of groups A1, A2, C1, C2, or D and another portion of the capture oligomer serves as one of a binding pair (ligand) to immobilize the captured HPV RNA on a solid support to facilitate separation of the captured HPV RNA from other sample components before the amplification step. One or more of the amplification oligomers used in the subsequent amplification reaction may be included in the HPV capturing step because the amplification oligomers hybridize to separate target sequences than those of the capture probe oligomers in the HPV RNA and do not interfere with target capture but provide a primer on the target for the initiation of the amplification reaction. A preferred embodiment uses a mixture of capture probes that include SEQ ID Nos. 2, 4, 6, 8, and 10. Other preferred embodiments use a mixture of capture probe oligomers that include the HPV-specific sequences of SEQ ID Nos. 2, 4, 6, 8, and 10 covalently linked to a 3' tail portion, as in a mixture of capture probes of SEQ ID Nos. 1, 3, 5, 7, and 9. The HPV-specific sequence of the capture probe hybridizes to the HPV target sequence and the tail portion hybridizes to a complementary sequence (oligo-dT) that is immobilized to a solid support. Preferably, the hybridizations of the capture step are performed with the capture oligomer and HPV target RNA free in solution to utilize the hybridization kinetics associated with solution phase nucleic acid hybridization. This hybridization produces a capture oligomer: HPV RNA complex that is then bound to an immobilized probe by hybridization of the tail portion of the capture oligomer with its complementary immobilized sequence and the resulting complex is separated from other sample components by using standard methods (e.g., filtration, centrifugation, magnetic separation). It will be understood by those skilled in the art that any binding pair ligand or set of complementary sequences between the tail portion and the immobilized probe may be used to perform the capture step. In preferred embodiments, the immobilized probe is oligo-dT attached to magnetically attractable monodisperse particles so that hybridization complexes containing HPV RNA are readily separated from solution by applying magnetic force to the vessel containing the reaction mixture. The captured HPV target RNA may be washed one or more times, further purifying the target from potential inhibitors (e.g., by resuspending particles with attached HPV RNA: capture oligomer:immobilized probe complexes in a washing solution and retrieving the particles with the attached complexes from the washing solution). To limit the number of handling steps, the HPV target nucleic acid may be amplified without releasing it from the capture oligomer. If amplification oligomers are present during the target capture step, then the initial amplification reaction (cDNA formation) may be accomplished by polymerization from the 3' ends of the amplification oligomers hybridized to the captured HPV target RNA.

Assays for HPV detection may optionally include a non-HPV internal control (IC) nucleic acid that is amplified and detected in the same assay reaction mixtures by using amplification and detection oligomers specific for the IC sequence that react under the same assay conditions to provide a positive signal that is distinguishable from an HPV-associated signal (e.g., a different AE label is used for the IC-specific probe compared to the HPV probes and the distinguishable signals are detected separately using well known methods (e.g., U.S. Pat. Nos. 5,658,737, 5,756,706, 5,827,656 and 5,840,873, Nelson et al.). Amplification and detection of a signal from the amplified IC sequence demonstrates that the assay reagents, conditions, and performance of assay steps were properly used in the assay if no signal is obtained for the HPV target (e.g., samples that test negative for the presence of HPV). The IC may be used as an internal calibrator for the assay when a quantitative result is desired, i.e., the signal obtained from the IC amplification and detection is used to set a parameter used in an algorithm for quantitating the amount of HPV nucleic acid in a sample based on the signal obtained for amplified HPV target sequences. A preferred embodiment of an IC is a randomized sequence that has been derived from a naturally occurring source (e.g., an HIV sequence that has been rearranged in a random manner). A preferred IC is an RNA transcript synthesized in vitro, e.g. transcripts made from a cloned randomized sequence, to provide an accurate amount of IC per reaction. Primers and a probe specific for the IC target sequence synthesized in vitro and used to amplify the IC target sequence and detect the amplified IC sequence by using substantially the same assay conditions used to amplify and detect the HPV sequences. In preferred embodiments that include a target capture step, the assay further includes a capture probe specific for the IC target in the same capture step used to purify the HPV targets, so that the IC is treated at every step in the assay in the assay in a manner analogous to that for the HPV analytes.

Amplifying the captured HPV target region can be accomplished using a variety of known nucleic acid amplification reactions, but preferably uses a transcription-associated amplification reaction. In such an embodiment, many strands of nucleic acid are produced from a single copy of target nucleic acid, thus permitting detection of the target by detecting probes that are bound to the amplified sequences. Transcription-associated amplification is performed at substantially isothermal conditions as described in detail previously (e.g., transcription mediated amplification (TMA) as described by Kacian et al. in U.S. Pat. Nos. 5,399,491 and 5,554,516, and nucleic acid sequence-based amplification (NASBA) as described by Davey et al. in U.S. Pat. No. 5,409,818). Briefly, transcription-associated amplification uses a promoter primer that contains a target-specific sequence and a promoter sequence for an RNA polymerase, another primer, enzymes to supply synthetic and degradative activities (reverse transcriptase (RT), DNA-dependent RNase, and RNA polymerase), substrates (deoxyribonucleoside triphosphates, ribonucleoside triphosphates) and appropriate salts, buffers, and cofactors in solution to produce multiple RNA transcripts from a nucleic acid template. Briefly, a promoter primer hybridizes specifically to its target RNA sequence and reverse transcriptase creates a first strand cDNA by extension from the 3' end of the promoter primer. The cDNA may be made available for hybridization with the second primer by using any method (e.g, denaturing the duplex), but preferably uses RNase H activity (e.g., supplied by RT enzyme) that digests the RNA strand in the cDNA:RNA duplex. The second primer binds to the cDNA and a new strand of DNA is synthesized from the 3' end of the second primer by using RT to create a double-stranded DNA having a functional promoter sequence at one end. RNA polymerase binds to the promoter sequence and transcribes multiple transcripts ("amplicons"). These amplicons are used in subsequent steps of the amplification process, each serving as a template for a new round of replication to generate large amounts of amplified nucleic acid (about 100 to 3,000 copies synthesized from each RNA template strand).

A promoter primer oligonucleotide contains a 5' promoter sequence that serves as a functional promoter when bound by the appropriate RNA polymerase, and a 3' sequence that hybridizes specifically to a target region sequence. Preferred embodiments include a T7 promoter sequence specific for T7 RNA polymerase. Preferred embodiments of promoter primers include those of SEQ ID Nos. 18, 20, 22, 24, 26, 28, 30, 32, 34, and 36, which are used in combination with primers of SEQ ID Nos. 38 to 41.

In transcription-mediated amplification of HPV sequences, the HPV RNA is hybridized to a promoter primer, e.g., one or more of SEQ ID Nos. 18, 20, 22, 24, 26, 28, 30, 32, 34, and 36, and by using the RT activity, a cDNA is synthesized from the promoter primer using the HPV RNA as the template. Then, the second primer, e.g., one or more of SEQ ID Nos. 38 to 41, hybridizes to the cDNA strand and RT-mediated polymerization forms a DNA duplex, thus forming a functional double-stranded promoter which bound by its specific RNA polymerase that transcribes RNA transcripts from the HPV sequence, making HPV amplification products. By repeating the hybridization and polymerization steps following the cDNA synthesis step, additional RNA transcripts are produced, thus producing HPV target-specific amplification products.

It will be appreciated that other in vitro nucleic acid amplification systems that use amplification oligomers (e.g., PCR or SDA) may be used to amplify the HPV target sequences, and these do not require a promoter sequence on a primer. For such amplification methods, preferred mixtures of amplification oligomers use first primer oligomers of SEQ ID Nos. 19, 21, 23, 25, 27, 29, 31, 33, 35, and 37 with second primer oligomers of SEQ ID Nos. 38 to 41.

The detecting step generally uses a mixture of HPV-specific probes for detection of any one of the target HPV types which may be present in the sample, i.e., when at least one probe binds specifically to an amplified HPV sequence (e.g., RNA transcripts or amplicons) a positive result is obtained. For assays that detect HPV types of groups A1, A2, C1, C2, and D, the detecting step uses a mixture of detection probes, preferably a mixture of SEQ ID Nos. 11 to 15 and 17 or SEQ ID Nos. 11, 12, 14, 15, 17, 44, 45 and 52. In assays that involve two or three amplification and detection reactions to detect the presence of any one of HPV types of groups A1, A2, C1, C2, and D on one reaction and to detect a subset of the HPV types such as HPV 16 and/or HPV 18 in another reaction, a single probe or subset of the probe mixture is used in the detecting step for the subset of the HPV types (e.g., SEQ ID NO:11, SEQ ID NO:13, or SEQ ID NO:44, individually or as a mixture of SEQ ID NO:11 and SEQ ID No. 13 or 44). Preferred embodiments use a labeled probe that produces a signal that is detected without purifying bound from unbound probes (i.e., in a homogeneous detection system). More preferably, the probe is labeled with an acridinium ester (AE) compound to produce a detectable chemiluminescent signal (U.S. Pat. Nos. 5,283,174 and 5,656,744, Arnold et al.; U.S. Pat. No. 5,658,737, Nelson et al.).

For the methods described herein, the capture oligomers, amplification oligomers and detection probes oligomers have specific sequences that have been identified as useful for detecting multiple types of HPV target sequences localized in the E6/E7 gene regions of HPV types 16, 18, 31, 33, 35, 39, 45, 51, 52, 56, 58, 59, and 68. Many oligomers were designed to hybridize to more than one HPV type in a genetically related group by selecting target sequences that are common to multiple HPV types or by creating consensus sequences that include common structural features of multiple HPV types but are not identical to all types, or even one type, in the targeted group. Embodiments of amplification oligomers are those of SEQ ID Nos. 18 to 42, and embodiments of detection probe oligomers are those of SEQ ID Nos. 11 to 17, 41, 44 to 54, and 58. For probes labeled with chemiluminescent compounds, additional oligomers that are substantially complementary to the probe oligomer may be hybridized to the probe oligomer to stabilize the labeled probe during storage, and embodiments of such probe protection oligomers are those of SEQ ID Nos. 59 to 64. Preferred embodiments of capture probe oligomers have the HPV target-binding sequences of SEQ ID Nos. 2, 4, 6, 8 and 10, which may be attached to any moiety that can serve as a binding partner (i.e., ligands such as biotin or avidin) for linking the target region sequences to a retrievable solid phase. Embodiments of capture probes may include a tail sequence that hybridizes to an immobilized complementary oligomer, as in those of SEQ ID Nos. 1, 3, 5, 7, and 9, which include a 3' tail sequence of $dT_3A_{30}$. These oligomers have generally been disclosed as contiguous DNA sequences, but it will be appreciated that their RNA equivalent sequences, or similar sequences that contain substitutions at one or more positions of base analogs (e.g., inosine) or synthetic purine and pyrimidine derivatives, such as P or K bases (Lin & Brown, 1989, *Nucl. Acids Res.* 17:10373-83; Lin & Brown, 1992, *Nucl. Acids Res.* 20: 5149-52), may function in substantially the same way. For oligomers that bind to RNA targets, embodiments may contain a 2'-methoxy backbone at one or more linkages in the nucleic acid backbone. Preferred embodiments synthesized with a 2'-methoxy backbone generally use RNA bases for positions linked by the 2'-methoxy backbone.

Embodiments of the invention include kits made up of various combinations of materials useful for performing the method steps for detection of HPV nucleic acids in a specimen. Preferred kits contain a amplification oligonucleotides that serve as primers for in vitro amplification of nucleic acid sequences of HPV types of groups A1, A2, C1, C2 and D. Exemplary kits include a first and a second amplification oligonucleotides that are complementary to opposite strands of the HPV target sequences and flank the ends of the HPV sequence to be amplified. Embodiments include amplification oligomers that contain the sequences of SEQ ID Nos. 18 or 19, 20 or 21, 22 or 23, 24 or 25, 26 or 27, 28 or 29, 30 or 31, 32 or 33, 34 or 35, and 36 or 37 as a first amplification oligomer, and sequences of SEQ ID Nos. 38 to 41 as the second amplification oligomer. The first amplification oligonucleotide is preferably up to 100 nt in length, more preferably is from 20 to 60 nt in length, in which the nucleotide bases complementary to the HPV target region sequence may include substitutions of one or more base analogs. The second amplification oligonucleotide is preferably up to 100 nt in length, more preferably is from about 15 to 25 nt in length, which may include of one or more nitrogenous base analogs. Kit embodiments may further contain one or more probe oligomers for detecting the HPV amplified products. Embodiments of these probes include oligomers of 11 to 17, 44 to 54 and 58, and preferably use probes of SEQ ID Nos. 11, 12, 14, 15, 17, 44, 45 and 52. Kits embodiments may further include additional oligomers, such as those of SEQ ID Nos. 57 and 59 to 64, packaged in a mixture with probe oligomers to stabilize functional components of the probe oligomers before use. Kits may also contain oligomers that serve as capture oligomers for purifying the target nucleic acid from a sample. Examples of capture oligomers for use in kits include those that contain about 25 to 30 nt complementary to HPV target sequences in the HPV E6/E7 gene region in HPV types of groups A1, A2, C1, C2 and D. Embodiments of capture oligomers included in kits preferably include those that contain the HPV-specific sequences of SEQ ID Nos. 2, 4, 6, 8, and 10 attached to a ligand that binds the capture oligomer to a solid support. Preferred embodiments of capture oligomers in kits include a mixture of oligomers of SEQ ID Nos. 1, 3, 5, 7 and 9, which include a substantially homopolymeric tail sequence attached to the 3' end of the HPV-specific sequences of SEQ ID Nos. 2, 4, 6, 8, and 10. It will be understood that embodiments of the kits described above embrace kits in which the oligomers consist of the complementary sequences of the specified sequences, RNA and DNA equivalents or RNA/DNA chimerics of the specified sequences, or substantially equivalent sequences that may contain one or more substitutions of nucleotide analogs in the specified sequences. It will also be understood that kit embodiments may include oligomers as individually packaged components, but preferably include mixtures of oligomers, e.g., a mixture of target capture and first amplification oligomers, or a mixture of probe oligomers. Kits useful for practicing the methods of the invention may include those that include any of the amplification oligomers and/or detection probes disclosed herein which are packaged in combination with each other. Kits may also include capture oligomers which may be packaged in combination with the amplification oligonucleotides and/or detection probes. Kits for practicing the methods of the invention may further include one or more reagents for use in methods steps of target capture, in vitro amplification, and/or detection of amplified products as described herein. It will be clear to those skilled in the art, that the present invention embraces many different kit configurations.

Oligomers described herein have been tested in assays that captured HPV RNA from samples by using a target capture step, amplified the captured HPV target sequences in a transcription-mediated amplification reaction, and detected the amplified sequences by using labeled detection probes in a homogeneous reaction to detected a chemiluminescent signal from bound probes to indicate the presence of HPV in the tested sample. The general method steps used in these assays have been described previously (U.S. Pat. Nos. 6,110,678, 6,280,952, and 6,534,273, Weisburg et al., related to target capture; U.S. Pat. Nos. 5,399,491 and 5,554,516, Kacian et al., related to transcription-mediated amplification; and U.S. Pat. Nos. 5,283,174 and 5,656,744, Arnold et al. and U.S. Pat. No. 5,658,737, Nelson et al., related to chemiluminescent labeling and detection).

In the HPV detection assays described herein, the following reagents were generally used. Sample Transport Solution contained 15 mM sodium phosphate monobasic, 15 mM sodium phosphate dibasic, 1 mM EDTA, 1 mM EGTA, and 110 mM lithium lauryl sulfate (LLS), at pH 6.7. Target Capture Reagent contained 250 mM HEPES, 310 mM lithium hydroxide, 1.88 M lithium chloride, 100 mM EDTA, at pH 6.4, and 250 µg/ml of magnetic particles (1 micron S$_{ERA}$-M$_{AG}$™ MG-CM particles, Seradyn, Inc. Indianapolis, Ind.) with $(dT)_{14}$ oligomers covalently bound thereto. Wash Solution contained 10 mM HEPES, 150 mM sodium chloride, 6.5 mM sodium hydroxide, 1 mM EDTA, 0.3% (v/v) ethanol, 0.02% (w/v) methyl paraben, 0.01% (w/v) propyl paraben, and 0.1% (w/v) sodium lauryl sulfate, at pH 7.5. Probe Reagent contained one or more labeled detection probes in a solution made up of 100 mM lithium succinate, 2% (w/v) LLS, 15 mM mercaptoethanesulfonate, 1.2 M lithium chloride, 20 mM EDTA, and 3% (v/v) ethanol, at pH 4.7. Amplification reagent is a concentrated mixture that was mixed with other reaction components to produce a mixture containing 47.6 mM Na-HEPES, 12.5 mM N-acetyl-L-cysteine, 2.5% TRITON™ X-100, 54.8 mM KCl, 23 mM $MgCl_2$, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM $Na_2EDTA$, 5% v/v glycerol, 2.9% trehalose, 0.225% ethanol, 0.075% methylparaben, 0.015% propylparaben, and 0.002% Phenol Red, at pH 7.5-7.6, although other formulations of amplification reagent may function equally well. Primers may be added to the amplification reagent or added to amplification reactions separate from the amplification reagent. Enzymes were Moloney Murine Leukemia Virus Reverse Transcriptase (MMLV-RT) and bacteriophage T7 RNA polymerase for which units are functionally defined as: 1 U of MMLV-RT incorporates 1 nmol of dTTP in 10 min at 37° C. using 200-400 micromolar oligo dT-primed poly(A) as template, and 1 U of T7 RNA polymerase incorporates 1 nmol of ATP into RNA in 1 hr at 37° C. using a DNA template containing a T7 promoter. Hybridization Reagent was made up of 100 mM succinic acid, 2% (w/v) LLS, 100 mM lithium hydroxide, 15 mM aldrithiol-2, 1.2 M lithium chloride, 20 mM EDTA, and 3.0% (v/v) ethanol, at pH 4.7. Selection Reagent was 600 mM boric acid, 182.5 mM sodium hydroxide, 1% (v/v) octoxynol (TRITON® X-100), at pH 8.5. Detection Reagents were Detect Reagent I, which contained 1 mM nitric acid and 32 mM hydrogen peroxide, and Detect Reagent II was 1.5 M sodium hydroxide. Oligomers in the HPV assays were generally used in the following concentrations: 2.5 pmol per reaction for each capture probe oligomer, 2.5 pmol per reaction for each promoter primer included in target capture reagent, 15 pmol per reaction for each non-promoter primer included in an amplification mixture, 1.25 pmol to 7.5 pmol per reaction of each promoter primer include in an amplification mixtures, and 0.03 pmol per reaction of each detection probe. For the tests performed, the HPV target generally was a transcript made in vitro containing all or part of the E6/E7 gene sequences of the HPV type(s) to be detected, used at a concentration of 25 to 100,000 copies per reaction, usually at 100 or 1000 copies per reaction. Additional details are provided in the examples that follow, which are representative of some of the embodiments of the present invention.

Example 1: Target Capture, Amplification and Detection of HPV E6/E7 Sequences

This example describes assay steps and conditions used in many tests that detected target sequences from HPV types 16, 18, 31, 33, 35, 39, 45, 51, 52, 56, 58, 59, and 68 in a sample.

In the target capture steps, a mixture of oligomers of SEQ ID Nos. 1, 3, 5, 7 and 9 (2.5 pmol each) were used in reactions containing 0.5 ml of target capture reagent containing 100 or 1,000 copies of HPV target RNA appropriate for each test (i.e., one or more E6/E7 transcripts of HPV types 16, 18, 31, 33, 35, 39, 45, 51, 52, 56, 58, 59, and 68). These reaction mixtures also contained 2.5 pmol each of oligomers of SEQ ID Nos. 18, 20, 22, 24, 26, 28, 30, 32, 34, and 36. The mixtures were incubated at 62° C. for 30 min, then at room temperature for 30 min to allow hybridization of the oligomers to the target sequences, then the hybridization complexes on the magnetic particles were separated from other reaction components by applying magnetic force to the outside of the vessel (about 5-10 min), other sample components were aspirated away, the hybridization complexes on the particles were washed with 1 ml of wash solution at room temperature and the hybridization complexes on the magnetic particles were separated from the wash solution by applying magnetic force and aspiration as described above.

The captured HPV target RNA in the hybridization complexes that include at least one T7 promoter primer were then used in amplification reactions, each containing 40 mM Trizma base, pH 7.5, 17.5 mM KCl, 20 mM $MgCl_2$, 5% polyvinylpyrrolidone (PVP), 1 mM each dNTP, 4 mM each rNTP, and 15 pmol per reaction each of oligomers of SEQ ID Nos. 38 to 41, and optimized amounts of the T7 primer oligomers per reaction as follows: SEQ ID NO:18 (1.25 pmol), SEQ ID NO:20 (7.5 pmol), SEQ ID NO:22 (1.25 pmol), SEQ ID NO:24 (2.5 pmol), SEQ ID NO:26 (2.5 pmol), SEQ ID NO:28 (2.5 pmol), SEQ ID NO:30 (2.5 pmol), SEQ ID NO:32 (7.5 pmol), SEQ ID NO:34 (1.25 pmol), and SEQ ID NO:36 (1.25 pmol). Reactions were covered with a layer (200 μl) of inert oil to prevent evaporation, and incubated at 62° C. for 10-15 min, and then at 42° C. for 3-5 min. Then, enzymes (about 750 U of MMLV RT and about 2000 U of T7 RNA polymerase per reaction) were added, mixed, and the amplification reactions were incubated at 42° C. for about 1 hr.

For detection of the amplified sequences, 0.1 ml of the probe reagent containing a mixture of oligomers of SEQ ID Nos. 11 to 16 or SEQ ID Nos. 11 to 15 and 17, each at 0.03 pmol per reaction and labeled with AE compounds, was added to the amplification mixture and incubated at 62° C. for about 20 min, then 0.25 ml of selection reagent was added and the mixture was incubated at 62° C. for about 10 min, and then the reaction was cooled to room temperature (about 15 min) and the chemiluminescence was produced from bound probes after adding the detection reagents I and II sequentially, substantially as described previously (U.S. Pat. No. 5,658,737 at column 25, lines 27-46; Nelson et al., 1996, *Biochem.* 35:8429-8438 at 8432), and the signals (relative light units or RLU) were detected (for 2 sec) by using a luminometer (Leader HC+, Gen-Probe Inc., San Diego, Calif.).

In a series of multiplex assays, target sequences of HPV types 16, 18, 31, 33, 35, 39, 45, 51, 52, 56, 58, 59, 68 were each amplified and detected using the assays described above using samples containing known amounts of each target (in a range of 25 to 1000 copies per reaction). All of the HPV types provided positive signals, generally in a range of about 650,000 RLU to over 2,000,000 RLU for samples that contained 200 or more copies of each of the target HPV RNA, although HPV types 31, 35, 18, 45, 59, and 68 provided positive signals (greater than 500,000 RLU) when as few as 25 copies of the target RNA was present in the sample. Based on the results, the approximate sensitivity of the multiplex assay was 25 copies per reaction for HPVs 18, 31, 35, 45, 51, 56, 59 and 68, 50 copies per reaction for HPV16, 200 copies per reaction for HPVs 33, 39 and 58, and 400 copies per reaction for HPV52.

To show that the multiplex assay did not cross react with HPV types that the assay was not designed to detect, i.e., low risk HPV types, the same multiple amplification and detection reaction steps were performed using as the target nucleic acids in vitro E6/E7 transcripts made from low risk HPV types 6, 11, 42, 43 and 44, used at 1,000,000 and 10,000,000 copies per reaction. That is, the low risk HPV types were tested at 1,000-fold to 10,000-fold more copies per reaction than for the high-risk HPV types of groups A1, A2, C1, C2, and D that the assay detected. The low risk HPV targets tested in the assay provided negative results compared to the positive controls (1000 copies of HPV16, 18, 33, 39 and 51 in vitro E6/E7 transcripts tested in individual reactions for each target HPV). The positive controls provided positive signals of greater than 1,000,000 to greater than 2,000,000 RLU, while the low risk HPV types provided negative signals (about 14,000 RLU or less).

Example 2: Amplification and Detection of HPV Types in Groups A2, C1, C2 and D

This example presents some of the tests done to demonstrate amplification and detection of individual HPV types in different groups using combinations of amplification and detection oligomers. The reactions were performed substantially as described above, using only amplification and detection steps to the efficiency of detecting target sequences in test samples that were made using known amounts of in vitro transcripts of the E7 regions (100 to 100,000 copies per reaction). Negative controls were samples tested identically but containing no target transcripts. Amplification reactions were performed individually for each group using the same amounts per reaction of each non-promoter primer (15 pmol) and each promoter primer (5 to 7.5 pmol) tested in the reactions for that group (shown by their SEQ ID NOs with the data tables that follow). The prepared samples containing known amounts of each HPV target RNA were mixed with amplification reagents (40 mM Trizma base, pH 7.5, 17.5 mM KCl, 20 mM $MgCl_2$, 5% polyvinylpyrrolidone (PVP), 1 mM each dNTP, 4 mM each rNTP) and each the amplification oligomers shown in the data tables that follow for each group. Reactions were covered with a layer of inert oil to prevent evaporation, incubated at 62° C. for 10-15 min, then at 42° C. for 3-5 min, and then enzymes (about 750 U of MMLV RT and about 2000 U of T7 RNA polymerase per reaction) were added, mixed, and the amplification reactions were incubated at 42° C. for about 1 hr. Following amplification, an aliquot of each of the amplification reactions was mixed with hybridization reagent and AE-labeled probes (100 fmol per reaction) of the sequences shown for the data tables that follow for each group, and the mixtures were incubated to allow hybridization of the probes to the amplified products (62° C. for about 20 min) and then selection reagent was added to inactivate the label on unbound probes (at 62° C. for about 10 min). The detection reaction mixtures were cooled to room temperature, Detect Reagents I and II were added sequentially to induce chemiluminescence from bound probes, and the chemiluminescent signals (RLU) were detected in a illuminometer substantially as described previously (U.S. Pat. No. 5,658,737; Nelson et al., 1996, *Biochem.* 35:8429-8438 at 8432). The results of tests for the HPV types of groups A2, C1, C2 and D are shown below.

TABLE 2

Group A2 Types: RLU Detected Following Amplification and Detection with Probe of SEQ ID NO: 12

| HPV targets | \multicolumn{5}{c}{Target Copies Per Reaction} | Primers |
|---|---|---|---|---|---|---|
| | 0 | 100 | 1,000 | 10,000 | 100,000 | |
| HPV33 | 3,438 | 7,900,599 | 7,850,985 | 8,184,822 | 8,006,992 | 24, 38 |
| | 3,035 | 18,198 | 91,184 | 2,448,776 | 6,805,674 | 26, 38 |
| | 3,962 | 7,870,920 | 7,875,748 | 7,768,868 | 7,778,976 | 24, 26, 38 |
| HPV58 | 5,520 | 10,386,537 | 10,413,923 | 10,593,322 | 10,651,717 | 24, 38 |
| | 4,656 | 13,533 | 21,115 | 129,118 | 1,021,726 | 26, 38 |
| | 2,945 | 5,002,410 | 5,429,599 | 5,637,786 | 5,743,310 | 24, 26, 38 |

TABLE 3

Group C1 Types: RLU Detected Following Amplification and Detection

| HPV targets | \multicolumn{5}{c}{Target Copies Per Reaction} | Primers/Probes |
|---|---|---|---|---|---|---|
| | 0 | 100 | 1,000 | 10,000 | 100,000 | |
| HPV45 | 5,502 | 2,288,692 | 8,243,285 | 10,191,401 | 10,036,303 | 28, 39/47 |
| HPV18 | 2,155 | 766,270 | 2,638,578 | 6,766,617 | 6,841,980 | 28, 39/44 |

TABLE 4

Group C2 Types: RLU Detected Following Amplification and Detection with Probe of SEQ ID NO: 14

| HPV targets | \multicolumn{5}{c}{Target Copies Per Reaction} | Primers |
|---|---|---|---|---|---|---|
| | 0 | 100 | 1,000 | 10,000 | 100,000 | |
| HPV39 | 5,793 | 9,782,945 | 9,771,588 | 9,784,294 | 9,432,972 | 32, 40 |
| HPV68 | 6,996 | 8,398,120 | 9,389,473 | 9,509,942 | 9,472,284 | 32, 40 |

TABLE 5

Group D Types: RLU Detected Following Amplification and Detection

| HPV targets | \multicolumn{5}{c}{Target Copies Per Reaction} | Primers/Probes |
|---|---|---|---|---|---|---|
| | 0 | 100 | 1,000 | 10,000 | 100,000 | |
| HPV51 | 7,157 | 7,199,400 | 8,956,784 | 9,128,567 | 9,100,401 | 34, 36, 41/15 |
| | 7,476 | 7,626,000 | 8,971,061 | 8,962,289 | 9,083,188 | 34, 41/15 |
| | 7,953 | 6,352,096 | 7,188,431 | 7,247,835 | 7,258,649 | 34, 36, 41/15, 16 |
| | 8,719 | 5,148,663 | 7,132,653 | 7,328,616 | 6,527,860 | 34, 41/15, 16 |
| HPV56 | 2,342 | 4,143,796 | 5,096,028 | 5,266,208 | 5,248,864 | 34, 36, 41/16 |
| | 3,263 | 4,975,678 | 5,050,576 | 5,245,685 | 5,242,688 | 34, 41/16 |

These results show that the selected oligomers are effective at amplification and detection of different HPV types within a group, often providing positive results with as few as 100 copies per reaction of the target RNA. Many similar tests were performed using other combinations of amplification and detection oligomers disclosed herein with their respective HPV target transcripts which also provided positive results with as few as 100 copies of target RNA per reaction and consistently provided positive results when 1000 copies of target RNA per reaction.

Example 3: Multiplex Assay to Amplify and Detect HPV Types of Groups A1, A2, C1, C2 and D This example shows results obtained with a multiplex assay similar to that described in Example 1 that detected HPV types 16, 18, 31, 33, 35, 39, 45, 51, 52, 56, 58, 59, 68. This multiplex assay further included an internal control (IC) RNA (a randomized non-HPV RNA sequence) that was simultaneously amplified and detected by using IC-specific primers and probe, to produce a distinguishable chemiluminescent signal under identical assay conditions as used to detect the HPV analytes.

In the target capture portion of the assay, a mixture of capture oligomers of SEQ ID NO:1 (0.65 pmol/µl) SEQ ID NO:3 and SEQ ID NO:9 (2.5 pmol/µl each), and SEQ ID NO:5 and SEQ ID NO:7 (0.5 pmol/µl each) were used in reactions containing target capture reagent and samples containing a known amount of HPV target RNA (in vitro transcripts of the E6/E7 gene region of HPV type 16, 18, 31, 33, 35, 39, 45, 51, 52, 56, 58, 59, or 68 at 100 to 1,000 copies per reaction). The capture reaction mixtures were incubated sequentially at 62° C. for 30 min and room temperature for 30 min to allow formation of hybridization complexes made up of HPV RNA:capture oligomer:immobilized probe on the solid support particles. The hybridization complexes on the particles were separated from other sample components by applying magnetic force to the outside of the vessel, aspirating other sample components away, and washing the hybridization complexes on the particles substantially as described above.

The captured HPV target RNA in the hybridization complexes were then amplified in a transcription mediated amplification reaction that included amplification reagent and amplification oligomers provided to the reaction from a mixture of promoter primers and a mixture of non-promoter primers. The promoter primers used were those of SEQ ID NO:18 (1.25 pmol/µl), SEQ ID NO:20 (7.5 pmol/µl), SEQ ID NO:22 (1.25 pmol/µl), SEQ ID NO:24 (7.5 pmol/µl), SEQ ID NO:26 (7.5 pmol/µl), SEQ ID NO:28 (2.5 pmol/µl), SEQ ID NO:30 (2.5 pmol/µl), SEQ ID NO:32 (7.5 pmol/µl), SEQ ID NO:34 (1.25 pmol/µl), and SEQ ID NO:36 (1.25 pmol/µl). The other primers were those of SEQ ID Nos. 38, 39, 40 and 41 (each at 15 pmol/µl). A promoter primer and primer specific for the internal control were also added to reactions that contained the internal control RNA. The mixtures were covered with a layer of inert oil to prevent evaporation, incubated sequentially at 62° C. for 10-15 min and 42° C. for about 5 min. Enzymes (MMLV RT and T7 RNA polymerase) were added, mixed, and the amplification reactions were incubated at 42° C. for about 60 min (45 to 75 min) substantially as described above.

For detection of the amplified HPV sequences, an aliquot of the amplification mixture was mixed with probe reagent and a mixture of probe oligomers of SEQ ID Nos. 11, 12, 14, 15, 17, 44, 45 and 52, each labeled with 2-methyl-AE and added in amounts to provide $1.5 \times 10^6$ RLU per reaction. Detection of the amplified internal control sequences used a synthetic oligomer specific for the internal control and labeled with a distinguishable AE compound (2'-fluoro-AE), added in an amount to provide $8.5 \times 10^5$ RLU per reaction. The detection mixtures were incubated at 62° C. for about 20 min, then cooled at room temperature for about 5 min, and selection reagent was added and the mixture was incubated at 62° C. for about 10 min, and then cooled to room temperature for about 15 min, when chemiluminescence was produced by using detection reagents I and II sequentially, and chemiluminescent signals (RLU) from the AE labels in bound probes were detected substantially as described above.

In these assays, a total of 10 replicate samples were tested for each of the HPV targets and copy numbers assayed, for which representative data is presented below for two different lots of amplification reagents used. The average RLU (mean) detected for the amplified target HPV sequences by type of the replicate reactions are shown along with the percentage of tests that were considered positive based on the detected RLU above background levels obtained in samples that contained no HPV target RNA that were treated identically. The results show that the multiplex assay detects HPV types 16, 18, 31, 33, 35, 39, 45, 51, 52, 56, 58, 59 and 68, although some variation in the results was observed (e.g., between individual specimens, performance of individual assays, or reagent lots). These results also show the relative sensitivity of the assay for the different HPV types tested.

TABLE 6

| HPV Type | Copies/reaction | Detected RLU (mean) | % Positive (n = 10) | Reagent Lot |
|---|---|---|---|---|
| 16 | 100 | 961,914 | 100 | 1 |
| 31 | 250 | 855,243 | 100 | 1 |
| 31 | 100 | 872,710 | 100 | 1 |
| 35 | 100 | 1,004,241 | 100 | 1 |
| 33 | 100 | 904,880 | 100 | 1 |
| 16 | 100 | 1,032,372 | 100 | 2 |
| 31 | 250 | 1,037,532 | 100 | 2 |
| 31 | 100 | 860,320 | 100 | 2 |
| 35 | 100 | 1,036,048 | 100 | 2 |
| 33 | 100 | 303,667 | 90 | 2 |
| 52 | 100 | 569,196 | 50 | 1 |
| 58 | 100 | 872,453 | 100 | 1 |
| 18 | 1000 | 526,424 | 100 | 1 |
| 18 | 500 | 383,899 | 90 | 1 |
| 56 | 250 | 736,253 | 100 | 1 |
| 52 | 100 | 26,251 | 0 | 2 |
| 58 | 100 | 184,647 | 60 | 2 |
| 18 | 1000 | 562,169 | 90 | 2 |
| 18 | 500 | 324,432 | 70 | 2 |
| 56 | 250 | 899,826 | 100 | 2 |
| 16 | 100 | 863,950 | 100 | 1 |
| 45 | 1000 | 100,368 | 20 | 1 |
| 45 | 500 | 43,731 | 10 | 1 |
| 59 | 1000 | 613,100 | 90 | 1 |
| 59 | 500 | 367,401 | 90 | 1 |
| 45 | 1000 | 382,050 | 100 | 2 |
| 45 | 500 | 264,810 | 100 | 2 |
| 59 | 1000 | 739,276 | 100 | 2 |
| 59 | 500 | 716,386 | 100 | 2 |
| 39 | 100 | 1,154,632 | 100 | 1 |
| 68 | 500 | 965,785 | 100 | 1 |
| 51 | 250 | 351,527 | 100 | 1 |
| 51 | 100 | 281,806 | 70 | 1 |
| 56 | 100 | 369,690 | 90 | 1 |
| 39 | 100 | 545,835 | 90 | 2 |
| 68 | 500 | 271,722 | 100 | 2 |
| 51 | 250 | 431,593 | 100 | 2 |
| 51 | 100 | 229,267 | 80 | 2 |
| 56 | 100 | 664,674 | 100 | 2 |

The above examples illustrate aspects and preferred embodiments of the invention which is claimed below.

We claim:

1. A detection reaction mixture comprising at least two detection probe oligomers,
   wherein a first detection probe oligomer comprises (a) a target-specific sequence selected from the group consisting of SEQ ID NO:11, a complement thereof, and an RNA equivalent thereof, and (b) a detectable label that is joined directly or indirectly to the nucleic acid sequence of (a); and
   wherein a second detection probe oligomer comprises (a') a target-specific sequence selected from the group consisting of SEQ ID NO:12, a complement thereof, and an RNA equivalent thereof, and (b') a detectable label that is joined directly or indirectly to the nucleic acid sequence of (a').

2. The detection reaction mixture of claim 1, further comprising at least one detection probe oligomer comprising a target-specific sequence selected from the group consisting of SEQ ID NO:14, SEQ ID NO:44, SEQ ID NO:45, SEQ ID NO:52, complements thereof, and RNA equivalents thereof.

3. The detection reaction mixture of claim 1, further comprising at least one detection probe oligomer comprising a target-specific sequence selected from the group consisting of SEQ ID NO:15, SEQ ID NO:17, complements thereof, and RNA equivalents thereof.

4. The detection reaction mixture of claim 1, wherein the detection reaction mixture further comprises a lithium salt selected from the group consisting of lithium succinate and lithium chloride.

5. The detection reaction mixture of claim 4, wherein the reaction mixture comprises both lithium succinate and lithium chloride.

6. The detection reaction mixture of claim 1, wherein the detection reaction mixture further comprises lithium lauryl sulfate.

7. The detection reaction mixture of claim 6, wherein the detection reaction mixture further comprises a lithium salt selected from the group consisting of lithium succinate and lithium chloride.

8. The detection reaction mixture of claim 1, wherein the detectable label is a chemiluminescent compound.

9. The detection reaction mixture of claim 8, wherein the chemiluminescent compound is an acridinium ester (AE) compound.

10. An aqueous formulation comprising:
    (a) at least one detection probe oligomer comprising (i) a target-specific sequence selected from the group consisting of SEQ ID NO:11, a complement thereof, and an RNA equivalent thereof, and (ii) a detectable label that is joined directly or indirectly to the nucleic acid sequence of (i);
    (b) a lithium salt selected from the group consisting of lithium succinate and lithium chloride;
    (c) lithium lauryl sulfate;
    (d) EDTA; and
    (e) ethanol.

11. The aqueous formulation of claim 10, wherein the lithium salt is lithium succinate.

12. The aqueous formulation of claim 11, further comprising lithium chloride.

13. The aqueous formulation of claim 10, wherein the lithium lauryl sulfate is present in the formulation at a concentration of 2% (w/v).

14. The aqueous formulation of claim 13, wherein the EDTA is present in the formulation at a concentration of 20 mM.

15. The aqueous formulation of claim 13, wherein the formulation further comprises 15 mM mercaptoethanesulfonate.

16. The aqueous formulation of claim 10, wherein the aqueous formulation further comprises a second detection probe oligomer comprising (i') a target-specific sequence selected from the group consisting of SEQ ID NO:12, a complement thereof, and an RNA equivalent thereof, and (ii') a detectable label that is joined directly or indirectly to the nucleic acid sequence of (i').

17. The aqueous formulation of claim 10, further comprising at least one detection probe oligomer comprising a target-specific sequence selected from the group consisting of SEQ ID NO:14, a complement thereof, and an RNA equivalent thereof.

18. The aqueous formulation of claim 10, further comprising at least one detection probe oligomer comprising a target-specific sequence selected from the group consisting of SEQ ID NO:44, a complement thereof, and an RNA equivalent thereof.

19. The aqueous formulation of claim 10, further comprising at least one detection probe oligomer comprising a target-specific sequence selected from the group consisting of SEQ ID NO:45, a complement thereof, and an RNA equivalent thereof.

20. The aqueous formulation of claim 10, further comprising at least one detection probe oligomer comprising a target-specific sequence selected from the group consisting of SEQ ID NO:52, a complement thereof, and an RNA equivalent thereof.

21. An aqueous formulation comprising:
    (a) one or both of (i) a detection probe oligomer comprising a target-specific sequence consisting of an RNA equivalent of SEQ ID NO:11, and (ii) a detection probe oligomer comprising a target-specific sequence consisting of an RNA equivalent of SEQ ID NO:12;
    (b) 100 mM lithium succinate;
    (c) 2% (w/v) lithium lauryl sulfate;
    (d) EDTA; and
    (e) ethanol.

22. The aqueous formulation of claim 21, further comprising 1.2 M lithium chloride.

23. The aqueous formulation of claim 22, further comprising 15 mM mercaptoethanesulfonate.

24. The aqueous formulation of claim 23, wherein the EDTA is present in the formulation at a concentration of 20 mM.

* * * * *

SEQUENCE LISTING

<160> NUMBER OF SEQ ID NOS: 64

<210> SEQ ID NO 1
<211> LENGTH: 61
<212> TYPE: DNA
<213> ORGANISM: Artificial Sequence
<220> FEATURE:
<223> OTHER INFORMATION: Synthetic target capture oligomer

<400> SEQUENCE: 1
gctcataaca gtggaggtca gttgcctctt taaaaaaaaa aaaaaaaaaa aaaaaaaaa    60 a    61

<210> SEQ ID NO 2
<211> LENGTH: 28
<212> TYPE: DNA
<213> ORGANISM: Artificial Sequence
<220> FEATURE:
<223> OTHER INFORMATION: Synthetic oligomer

<400> SEQUENCE: 2
gctcataaca gtggaggtca gttgcctc    28

<210> SEQ ID NO 3
<211> LENGTH: 58
<212> TYPE: DNA
<213> ORGANISM: Artificial sequence
<220> FEATURE:
<223> OTHER INFORMATION: Synthetic target capture oligomer

<400> SEQUENCE: 3
ctccaacacg ctgcacagcg ccctgtttaa aaaaaaaaa aaaaaaaaa aaaaaaa    58

<210> SEQ ID NO 4
<211> LENGTH: 25
<212> TYPE: DNA
<213> ORGANISM: Artificial
<220> FEATURE:
<223> OTHER INFORMATION: Synthetic oligomer

<400> SEQUENCE: 4
ctccaacacg ctgcacagcg ccctg    25

<210> SEQ ID NO 5
<211> LENGTH: 62
<212> TYPE: DNA
<213> ORGANISM: Artificial sequence
<220> FEATURE:
<223> OTHER INFORMATION: Synthetic target capture oligomer

<400> SEQUENCE: 5
gtgcacagat caggtagctt gtagggtcgt ttaaaaaaaa aaaaaaaaaa aaaaaaaaaa    60
aa    62

<210> SEQ ID NO 6
<211> LENGTH: 29
<212> TYPE: DNA
<213> ORGANISM: Artificial sequence
<220> FEATURE:
<223> OTHER INFORMATION: Synthetic oligomer

<400> SEQUENCE: 6
gtgcacagat caggtagctt gtagggtcg    29

<210> SEQ ID NO 7
<211> LENGTH: 60
<212> TYPE: DNA
<213> ORGANISM: Artificial sequence
<220> FEATURE:
<223> OTHER INFORMATION: Synthetic oligomer

```
<400> SEQUENCE: 7
gcacaggtct ggcaatttgt atggccgttt aaaaaaaaaa aaaaaaaaaa aaaaaaaaaa          60

<210> SEQ ID NO 8
<211> LENGTH: 27
<212> TYPE: DNA
<213> ORGANISM: Artificial sequence
<220> FEATURE:
<223> OTHER INFORMATION: Synthetic oligomer

<400> SEQUENCE: 8
gcacaggtct ggcaatttgt atggccg                                              27

<210> SEQ ID NO 9
<211> LENGTH: 59
<212> TYPE: DNA
<213> ORGANISM: Artificial sequence
<220> FEATURE:
<223> OTHER INFORMATION: Synthetic target capture oligomer

<400> SEQUENCE: 9
ggtctttgac atctgtgaca ccttattta aaaaaaaaaa aaaaaaaaaa aaaaaaaaa            59

<210> SEQ ID NO 10
<211> LENGTH: 26
<212> TYPE: DNA
<213> ORGANISM: Artificial sequence
<220> FEATURE:
<223> OTHER INFORMATION: Synthetic oligomer

<400> SEQUENCE: 10
ggtctttgac atctgtgaca ccttat                                               26

<210> SEQ ID NO 11
<211> LENGTH: 23
<212> TYPE: DNA
<213> ORGANISM: Artificial sequence
<220> FEATURE:
<223> OTHER INFORMATION: Synthetic oligomer

<400> SEQUENCE: 11
cagctggaca agcagaaccg gac                                                  23

<210> SEQ ID NO 12
<211> LENGTH: 21
<212> TYPE: DNA
<213> ORGANISM: Artificial sequence
<220> FEATURE:
<223> OTHER INFORMATION: Synthetic oligomer

<400> SEQUENCE: 12
ggccagatgg acaagcacaa c                                                    21

<210> SEQ ID NO 13
<211> LENGTH: 20
<212> TYPE: DNA
<213> ORGANISM: Artificial sequence
<220> FEATURE:
<223> OTHER INFORMATION: Synthetic oligomer

<400> SEQUENCE: 13
tgtgtgtgtg ttgtaagtgt                                                      20

<210> SEQ ID NO 14
<211> LENGTH: 21
```

```
<212> TYPE: DNA
<213> ORGANISM: Artificial sequence
<220> FEATURE:
<223> OTHER INFORMATION: Synthetic oligomer

<400> SEQUENCE: 14
ccgaccatgc agttaatcac c                                             21

<210> SEQ ID NO 15
<211> LENGTH: 21
<212> TYPE: DNA
<213> ORGANISM: Artificial sequence
<220> FEATURE:
<223> OTHER INFORMATION: Synthetic oligomer

<400> SEQUENCE: 15
gcgtgaccag ctaccagaaa g                                             21

<210> SEQ ID NO 16
<211> LENGTH: 21
<212> TYPE: DNA
<213> ORGANISM: Artificial sequence
<220> FEATURE:
<223> OTHER INFORMATION: Synthetic oligomer

<400> SEQUENCE: 16
gccacagcaa gctagacaag c                                             21

<210> SEQ ID NO 17
<211> LENGTH: 20
<212> TYPE: DNA
<213> ORGANISM: Artificial sequence
<220> FEATURE:
<223> OTHER INFORMATION: Synthetic oligomer

<400> SEQUENCE: 17
cacgtacctt gttgtgagtg                                               20

<210> SEQ ID NO 18
<211> LENGTH: 51
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 18
aatttaatac gactcactat agggagagaa gcgtagagtc acacttgcaa c            51

<210> SEQ ID NO 19
<211> LENGTH: 22
<212> TYPE: DNA
<213> ORGANISM: Artificial sequence
<220> FEATURE:
<223> OTHER INFORMATION: Synthetic oligomer

<400> SEQUENCE: 19
agcgtagagt cacacttgca ac                                            22

<210> SEQ ID NO 20
<211> LENGTH: 57
<212> TYPE: DNA
<213> ORGANISM: Artificial sequence
<220> FEATURE:
<223> OTHER INFORMATION: Synthetic oligomer
```

```
<220> FEATURE:
<221> NAME/KEY: Promoter
<222> LOCATION: (1)..(27)

<400> SEQUENCE: 20
aatttaatac gactcactat agggagacac acaaacgaag tgtagactta cactgac        57

<210> SEQ ID NO 21
<211> LENGTH: 30
<212> TYPE: DNA
<213> ORGANISM: Artificial sequence
<220> FEATURE:
<223> OTHER INFORMATION: Synthetic oligomer

<400> SEQUENCE: 21
cacacaaacg aagtgtagac ttacactgac                                      30

<210> SEQ ID NO 22
<211> LENGTH: 54
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 22
aatttaatac gactcactat agggagagtg tcgcctcaca tttacaacag gacg            54

<210> SEQ ID NO 23
<211> LENGTH: 27
<212> TYPE: DNA
<213> ORGANISM: Artificial sequence
<220> FEATURE:
<223> OTHER INFORMATION: Synthetic oligomer

<400> SEQUENCE: 23
gtgtcgcctc acatttacaa caggacg                                         27

<210> SEQ ID NO 24
<211> LENGTH: 53
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 24
aatttaatac gactcactat agggagagtt acaatgtagt aatcagctgt ggc             53

<210> SEQ ID NO 25
<211> LENGTH: 26
<212> TYPE: DNA
<213> ORGANISM: Artificial sequence
<220> FEATURE:
<223> OTHER INFORMATION: Synthetic oligomer

<400> SEQUENCE: 25
gttacaatgt agtaatcagc tgtggc                                          26

<210> SEQ ID NO 26
<211> LENGTH: 51
<212> TYPE: DNA
<213> ORGANISM: Artificial sequence
```

```
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 26
aatttaatac gactcactat agggagacac aatgtagtaa ttacttgtgg c       51

<210> SEQ ID NO 27
<211> LENGTH: 24
<212> TYPE: DNA
<213> ORGANISM: Artificial sequence
<220> FEATURE:
<223> OTHER INFORMATION: Synthetic oligomer

<400> SEQUENCE: 27
cacaatgtag taattacttg tggc                                     24

<210> SEQ ID NO 28
<211> LENGTH: 50
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 28
aatttaatac gactcactat agggagagca caccacggac acacaaagga         50

<210> SEQ ID NO 29
<211> LENGTH: 23
<212> TYPE: DNA
<213> ORGANISM: Artificial sequence
<220> FEATURE:
<223> OTHER INFORMATION: Synthetic oligomer

<400> SEQUENCE: 29
gcacaccacg gacacacaaa gga                                      23

<210> SEQ ID NO 30
<211> LENGTH: 54
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 30
aatttaatac gactcactat agggagagga tagtgtgtcc ataaacagct gctg    54

<210> SEQ ID NO 31
<211> LENGTH: 27
<212> TYPE: DNA
<213> ORGANISM: Artificial sequence
<220> FEATURE:
<223> OTHER INFORMATION: Synthetic oligomer

<400> SEQUENCE: 31
ggatagtgtg tccataaaca gctgctg                                  27

<210> SEQ ID NO 32
<211> LENGTH: 48
```

```
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 32
aatttaatac gactcactat agggagaccg tctggctagt agttgatg          48

<210> SEQ ID NO 33
<211> LENGTH: 21
<212> TYPE: DNA
<213> ORGANISM: Artificial sequence
<220> FEATURE:
<223> OTHER INFORMATION: Synthetic oligomer

<400> SEQUENCE: 33
ccgtctggct agtagttgat g                                       21

<210> SEQ ID NO 34
<211> LENGTH: 54
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 34
aatttaatac gactcactat agggagacca ctgccagttg tactacactt gaac    54

<210> SEQ ID NO 35
<211> LENGTH: 27
<212> TYPE: DNA
<213> ORGANISM: Artificial sequence
<220> FEATURE:
<223> OTHER INFORMATION: Synthetic oligomer

<400> SEQUENCE: 35
ccactgccag ttgtactaca cttgaac                                 27

<210> SEQ ID NO 36
<211> LENGTH: 54
<212> TYPE: DNA
<213> ORGANISM: Artificial sequence
<220> FEATURE:
<223> OTHER INFORMATION: Synthetic oligomer
<220> FEATURE:
<221> NAME/KEY: Promoter
<222> LOCATION: (1)..(27)

<400> SEQUENCE: 36
aatttaatac gactcactat agggagactc tgaatgtcca actgcaccac aaac    54

<210> SEQ ID NO 37
<211> LENGTH: 27
<212> TYPE: DNA
<213> ORGANISM: Artificial sequence
<220> FEATURE:
<223> OTHER INFORMATION: Synthetic oligomer

<400> SEQUENCE: 37
ctctgaatgt ccaactgcac cacaaac                                 27
```

```
<210> SEQ ID NO 38
<211> LENGTH: 21
<212> TYPE: DNA
<213> ORGANISM: Artificial sequence
<220> FEATURE:
<223> OTHER INFORMATION: Synthetic oligomer

<400> SEQUENCE: 38
gtgacagctc agatgaggat g                                              21

<210> SEQ ID NO 39
<211> LENGTH: 16
<212> TYPE: DNA
<213> ORGANISM: Artificial sequence
<220> FEATURE:
<223> OTHER INFORMATION: Synthetic oligomer

<400> SEQUENCE: 39
cgacgagccg aaccac                                                    16

<210> SEQ ID NO 40
<211> LENGTH: 19
<212> TYPE: DNA
<213> ORGANISM: Artificial sequence
<220> FEATURE:
<223> OTHER INFORMATION: Synthetic oligomer

<400> SEQUENCE: 40
gaccttgtat gtcacgagc                                                 19

<210> SEQ ID NO 41
<211> LENGTH: 22
<212> TYPE: DNA
<213> ORGANISM: Artificial sequence
<220> FEATURE:
<223> OTHER INFORMATION: Synthetic oligomer

<400> SEQUENCE: 41
gacagctcag aggaggagga tg                                             22

<210> SEQ ID NO 42
<211> LENGTH: 24
<212> TYPE: DNA
<213> ORGANISM: Artificial sequence
<220> FEATURE:
<223> OTHER INFORMATION: Synthetic oligomer

<400> SEQUENCE: 42
gaagcgtaga gtcacacttg caac                                           24

<210> SEQ ID NO 43
<211> LENGTH: 27
<212> TYPE: DNA
<213> ORGANISM: Bacteriophage T7
<220> FEATURE:
<221> NAME/KEY: Promoter
<222> LOCATION: (1)..(27)

<400> SEQUENCE: 43
aatttaatac gactcactat agggaga                                        27

<210> SEQ ID NO 44
<211> LENGTH: 25
<212> TYPE: DNA
<213> ORGANISM: Artificial sequence
<220> FEATURE:
<223> OTHER INFORMATION: Synthetic oligomer
```

<400> SEQUENCE: 44
gtagtagaaa gctcagcaga cgacc                                              25

<210> SEQ ID NO 45
<211> LENGTH: 21
<212> TYPE: DNA
<213> ORGANISM: Artificial sequence
<220> FEATURE:
<223> OTHER INFORMATION: Synthetic oligomer

<400> SEQUENCE: 45
gtagagagct cggcagagga c                                                  21

<210> SEQ ID NO 46
<211> LENGTH: 21
<212> TYPE: DNA
<213> ORGANISM: Artificial sequence
<220> FEATURE:
<223> OTHER INFORMATION: Synthetic oligomer
<220> FEATURE:
<221> NAME/KEY: misc_feature
<222> LOCATION: (18)..(18)
<223> OTHER INFORMATION: n is a or g or c or t or inosine

<400> SEQUENCE: 46
gtagagagct cggcaganga c                                                  21

<210> SEQ ID NO 47
<211> LENGTH: 22
<212> TYPE: DNA
<213> ORGANISM: Artificial sequence
<220> FEATURE:
<223> OTHER INFORMATION: Synthetic oligomer

<400> SEQUENCE: 47
gaccttagaa cactacagca gc                                                 22

<210> SEQ ID NO 48
<211> LENGTH: 20
<212> TYPE: DNA
<213> ORGANISM: Artificial sequence
<220> FEATURE:
<223> OTHER INFORMATION: Synthetic oligomer

<400> SEQUENCE: 48
gtgtgacggc agaattgagc                                                    20

<210> SEQ ID NO 49
<211> LENGTH: 25
<212> TYPE: DNA
<213> ORGANISM: Artificial sequence
<220> FEATURE:
<223> OTHER INFORMATION: Synthetic oligomer

<400> SEQUENCE: 49
cttcagctag tagtagaaac ctcgc                                              25

<210> SEQ ID NO 50
<211> LENGTH: 27
<212> TYPE: DNA
<213> ORGANISM: Artificial sequence
<220> FEATURE:
<223> OTHER INFORMATION: Synthetic oligomer

<400> SEQUENCE: 50
cagctagtag tagaaacctc gcaagac                                27

<210> SEQ ID NO 51
<211> LENGTH: 28
<212> TYPE: DNA
<213> ORGANISM: Artificial sequence
<220> FEATURE:
<223> OTHER INFORMATION: Synthetic oligomer

<400> SEQUENCE: 51
agctagtagt agaaacctcg caagacgg                               28

<210> SEQ ID NO 52
<211> LENGTH: 23
<212> TYPE: DNA
<213> ORGANISM: Artificial sequence
<220> FEATURE:
<223> OTHER INFORMATION: Synthetic oligomer

<400> SEQUENCE: 52
gtagtagaaa cctcgcaaga cgg                                    23

<210> SEQ ID NO 53
<211> LENGTH: 20
<212> TYPE: DNA
<213> ORGANISM: Artificial sequence
<220> FEATURE:
<223> OTHER INFORMATION: Synthetic oligomer

<400> SEQUENCE: 53
gtagaaacct cgcaagacgg                                        20

<210> SEQ ID NO 54
<211> LENGTH: 20
<212> TYPE: DNA
<213> ORGANISM: Artificial sequence
<220> FEATURE:
<223> OTHER INFORMATION: Synthetic oligomer

<400> SEQUENCE: 54
gcaagacgga ttgcgagcct                                        20

<210> SEQ ID NO 55
<211> LENGTH: 43
<212> TYPE: DNA
<213> ORGANISM: Artificial sequenc
<220> FEATURE:
<223> OTHER INFORMATION: Synthetic oligomer

<400> SEQUENCE: 55
cttcagctag tagtagaaac ctcgcaagac ggattgcgag cct              43

<210> SEQ ID NO 56
<211> LENGTH: 13
<212> TYPE: DNA
<213> ORGANISM: Artificial sequence
<220> FEATURE:
<223> OTHER INFORMATION: Synthetic oligomer

<400> SEQUENCE: 56
gtagaaacct cgc                                               13

<210> SEQ ID NO 57
<211> LENGTH: 15
<212> TYPE: DNA
<213> ORGANISM: Artificial sequence
<220> FEATURE:
<223> OTHER INFORMATION: Synthetic oligomer

<400> SEQUENCE: 57
ctgcttgtcc agctg                                           15

<210> SEQ ID NO 58
<211> LENGTH: 22
<212> TYPE: DNA
<213> ORGANISM: Artificial sequence
<220> FEATURE:
<223> OTHER INFORMATION: Synthetic oligomer

<400> SEQUENCE: 58
gagcaatttg acagctcaga gg                                   22

<210> SEQ ID NO 59
<211> LENGTH: 15
<212> TYPE: DNA
<213> ORGANISM: Artificial sequence
<220> FEATURE:
<223> OTHER INFORMATION: Synthetic oligomer

<400> SEQUENCE: 59
gcttgtccat ctggc                                           15

<210> SEQ ID NO 60
<211> LENGTH: 16
<212> TYPE: DNA
<213> ORGANISM: Artificial sequence
<220> FEATURE:
<223> OTHER INFORMATION: Synthetic oligomer

<400> SEQUENCE: 60
gattaactgc atggtc                                          16

<210> SEQ ID NO 61
<211> LENGTH: 15
<212> TYPE: DNA
<213> ORGANISM: Artificial sequence
<220> FEATURE:
<223> OTHER INFORMATION: Synthetic oligomer

<400> SEQUENCE: 61
ctggtagctg gtcac                                           15

<210> SEQ ID NO 62
<211> LENGTH: 16
<212> TYPE: DNA
<213> ORGANISM: Artificial sequence
<220> FEATURE:
<223> OTHER INFORMATION: Synthetic oligomer

<400> SEQUENCE: 62
tcacaacaag gtacgt                                          16

<210> SEQ ID NO 63
<211> LENGTH: 18
<212> TYPE: DNA
<213> ORGANISM: Artificial sequenc
<220> FEATURE:
<223> OTHER INFORMATION: Synthetic oligomer

<400> SEQUENCE: 63
cgtctgctga gctttcta                                        18

```
<210> SEQ ID NO 64
<211> LENGTH: 15
<212> TYPE: DNA
<213> ORGANISM: Artificial sequence
<220> FEATURE:
<223> OTHER INFORMATION: Synthetic oligomer

<400> SEQUENCE: 64
cttgcgaggt ttcta                                                    15
```